United States Patent [19]
Anolick et al.

[11] Patent Number: 5,663,255
[45] Date of Patent: Sep. 2, 1997

[54] AMORPHOUS TETRAFLUOROETHYLENE-HEXAFLUOROPROPYLENE COPOLYMERS

[75] Inventors: Colin Anolick; Robert Clayton Wheland, both of Wilmington, Del.

[73] Assignee: E. I. Du Pont de Nemours and Company, Wilmington, Del.

[21] Appl. No.: 549,407

[22] Filed: Oct. 27, 1995

Related U.S. Application Data

[63] Continuation-in-part of Ser. No. 384,068, Feb. 6, 1995, Pat. No. 5,478,905.

[51] Int. Cl.$^6$ ............................................. C08F 14/18
[52] U.S. Cl. ............................................................. 526/254
[58] Field of Search ................................ 526/254, 206, 526/217

[56] References Cited

U.S. PATENT DOCUMENTS

| | | | |
|---|---|---|---|
| 2,963,468 | 12/1960 | Cleaver | 260/87.5 |
| 3,051,677 | 8/1962 | Rexford | 260/29.6 |
| 3,062,793 | 11/1962 | Eleuterio | 260/87.5 |
| 3,287,339 | 11/1966 | Sianesi et al. | 260/92.1 |
| 3,817,951 | 6/1974 | Robinson | 526/254 |
| 4,001,351 | 1/1977 | Roura | 260/900 |
| 4,105,716 | 8/1978 | Sakai et al. | 260/884 |
| 4,123,603 | 10/1978 | Stewart, Jr. | 526/254 |
| 4,696,989 | 9/1987 | Oka et al. | 526/254 |
| 4,985,520 | 1/1991 | Hayashi et al. | 526/254 |
| 5,175,223 | 12/1992 | Brinati et al. | 526/254 |
| 5,543,217 | 8/1996 | Morgan | 526/254 |

FOREIGN PATENT DOCUMENTS

| | | | |
|---|---|---|---|
| 0 150 953 | 8/1985 | European Pat. Off. | C08F 8/50 |
| 0197562 | 10/1986 | European Pat. Off. | 526/254 |
| 2358270 | 5/1974 | Germany | 526/254 |
| 50-81882 | 7/1975 | Japan | C08F 8/12 |
| 60-81213 | 5/1985 | Japan | 526/254 |
| 1 348 354 | 10/1987 | U.S.S.R. | C08L 23/02 |
| 0888765 | 2/1962 | United Kingdom | 526/254 |
| 0894649 | 4/1962 | United Kingdom | 526/254 |

OTHER PUBLICATIONS

Hackh's Chemical Dictionary–Mar. 1981 p. 688.

*Primary Examiner*—Joseph L. Schofer
*Assistant Examiner*—N. Sarofim

[57] ABSTRACT

Disclosed herein are novel amorphous tetrafluoroethylene-hexafluoropropylene (TFE-HFP) copolymers, which are more random than previous amorphous TFE-HFP copolymers, as well as a novel high productivity continuous process for making these polymers. The polymers are particularly useful in the form of coatings, films and encapsulants.

12 Claims, 1 Drawing Sheet

AMORPHOUS TETRAFLUOROETHYLENE-HEXAFLUOROPROPYLENE COPOLYMERS

This application is a continuation of Ser. No. 08/384,068, filed Feb. 6, 1995, U.S. Pat. No. 5,478,905.

FIELD OF THE INVENTION

This invention concerns tetrafluoroethylene/hexafluoropropylene copolymers which are amorphous. They may be produced by a novel high pressure continuous process.

TECHNICAL BACKGROUND

Amorphous perfluorinated polymers are highly useful, particularly as coatings and encapsulants, because of their unusual surface properties, low refractive index, low dielectric constant, and the relative ease of coating or encapsulating objects with such polymers. However, the use of such polymers has been limited because of their high cost, which usually derives from the high cost of the monomers and/or the high cost of the polymerization process to make the polymers. Therefore, such polymers, and the processes for making them, which are lower in cost are constantly being sought.

U.S. Pat. No. 3,062,793 describes amorphous copolymers of tetrafluoroethylene (TFE) and hexafluoropropylene (HFP) which are made by a high pressure free radical polymerization. The only process described therein is a batch process which has a relatively low productivity.

SUMMARY OF THE INVENTION

This invention concerns a continuous polymerization process, comprising, contacting at a pressure of about 41 MPa to about 690 MPa, and a temperature above about 200° C., preferably about 200° C. to about 400° C., tetrafluoroethylene, hexafluoropropylene, and a radical initiator, to produce an amorphous polymer which contains at least 30 mole percent of repeat units derived from said hexafluoropropylene, at least 1 mole percent of repeat units derived from said tetrafluoroethylene, and provided that said continuous polymerization has an average residence time of about 10 seconds to about 30 minutes.

This invention also concerns an amorphous polymer, consisting essentially of repeat units of the formula:

(a) at least about 30 mole percent of

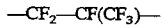   (I)

(b) at least about 1 mole percent

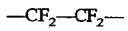   (II)

and (c) 0 to about 10 mole percent

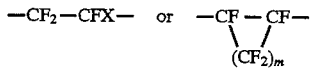   (III)

wherein X is $-C_nF_{2n+1}$ or $-OC_nF_{2n+1}$, m is 2, 3 or 4, and n is either an integer of 2 to 20 with alkyl groups $-C_nF_{2n+1}$ or an integer of 1–20 with alkoxy groups $-OC_nF_{2n+1}$.

provided that in said polymer less than 20 mole percent of (I) is present in the form of triads.

The invention also concerns a continuous polymerization process, comprising, contacting at a pressure of about 41 MPa to about 690 MPa, and a temperature of about 200° C. to about 400° C., tetrafluoroethylene, hexafluoropropylene, and a third monomer and a radical initiator, to produce an amorphous polymer which contains at least 30 mole percent of repeat units derived from said hexafluoropropylene, at least 0–70 mole percent of repeat units derived from said tetrafluoroethylene, and 0–70 mole percent of repeat units derived from said third monomer, and provided that said continuous polymerization has an average residence time of about 5 seconds to about 30 minutes.

DETAILS OF THE INVENTION

The TFE/HFP copolymer made herein is amorphous. By an amorphous polymer is meant that the polymer has a heat of melting of less than 1 J/g when measured by Differential Scanning Calorimetry (DSC) at a heating rate of 10° C./min, in the case of a TFE/HFP dipolymer. This is measured on a "first heat", that is virgin polymer is heated to at least 300° C. in the DSC (at 10° C./min), and the heat of melting, if any, is measured. In the case of terpolymers, where the residual third monomer is often removed from the polymer by heating for about four hours, at 150° C., in a vacuum oven, DSC "second heats", at 10° C./min to at least 200° C., were used.

These polymers are made via a continuous polymerization process in which the initial ingredients are fed to the reactor in an essentially continuous manner and in which the product stream is essentially continuously withdrawn at approximately the same rate at which the ingredients are added. Such types of reactions are generally known to the artisan, see for instance H. F. Mark, et at., Ed., Kirk-Othmer Encyclopedia of Chemical Technology, 3rd Ed., vol. 19, John Wiley & Sons, New York, 1982, p. 880–914. Such continuous reactors include continuous stirred tank reactors and pipeline (tubular) reactors. Under the conditions employed in the process as described herein, the productivity of the process is exceptionally high. By productivity herein is meant the weight of polymer produced in a unit volume of reactor in a unit volume of time. Productivities herein are reported as kg/L/hr.

The process described herein has typical productivities of about 0.8 to about 15 kg/L/hr. The Examples illustrate that typically higher polymerization temperatures give higher productivities. By contrast, a batch polymerization, making a somewhat similar polymer, reported in U.S. Pat. No. 3,062,793, has productivities (from the Examples) of about 0.01 to about 0.03 kg/L/hr, more than an order of magnitude less than that for the continuous process. This means a lower cost for polymer produced by the continuous process.

The process is run at a pressure of about 41 to about 690 MPa (~6,000 to ~100,000 psi), preferably about 55 to about 172 MPa (~8,000 to ~25,000 psi), more preferably about 62 to about 152 MPa (~9,000 to about 22,000 psi), and especially preferably about 69 to about 103 MPa (~10,000 to ~15,000 psi). As pressure drops down towards 41 MPa the molecular weight of the polymers formed and the conversion of monomers to polymer both tend to drop.

It is preferred that solvents not be used in the process, since at these pressures the monomers, particularly HFP, usually dissolve the polymer. Nonetheless, solvents can be used in the reactor. If the final product is to be a polymer solution, making the polymer solution directly may be preferable, to reduce costs (see Example 43). Sometimes for convenience in handling, small quantities of initiator are best introduced when diluted to a larger volume with a small amount of solvent (see Example 51). Solvent may also be used for other reasons, such as to decrease the viscosity of the process mixture, or to help keep lines clear of polymer, particularly at lower pressures. When solvents are used it is preferred that they be essentially inert under process conditions. Useful solvents include perfluorodimethylcyclobutane and perfluoro(n-butyltetrahydrofuran).

The polymer is soluble in the monomer(s) under the process conditions. Therefore, one method of polymer isolation is to reduce the pressure below that required for solution of the polymer, and isolate the polymer from that, as by decantation, filtration or centrifugation. Indeed, it may not be necessary to reduce the pressure of the unreacted monomers to atmospheric pressure, but merely that required for phase separation of the polymer. Therefore these monomers can be recycled with only a "partial" repressurization, thereby saving energy costs. Alternatively the pressure can be reduced to atmospheric pressure, while the volatile monomers are vented off, leaving the product polymer. The monomers can of course be recovered and reused.

The apparatus for running the polymerization may be any suitable pressure apparatus in which the reactant and products streams may be added and removed at appropriate rates. Thus the apparatus may be a stirred or unstirred autoclave, a pipeline type reactor, or other suitable apparatus. Agitation is not necessary, but preferable, especially to obtain polymers with low MWD's. The material of construction should be suitable for the process ingredients, and metals such as stainless steel are often suitable.

The polymerization is carried out above about 200° C., preferably from about 200° to about 400° C., more preferably from about 225° to about 400° C., and most preferably from about 250° to about 400° C. The initiator is chosen so that it will generate active free radicals at the temperature at which the polymerization is carried out. Such free radical sources, particularly those suitable for hydrocarbon vinyl monomers at much lower temperatures, are known to the artisan, see for instance J. Brandrup, et al., Ed., Polymer Handbook, 3rd Ed., John Wiley & Sons, New York, 1989, p. II/1 to II/65. The preferred temperature for running our process depends on both the monomers and the initiator and is often a compromise between raising temperature to favor high productivities and high conversions and lowering temperature to minimize chain transfer and monomer degradation. For the copolymerization of HFP with TFE, for example, where chain transfer is not a problem, $C_2F_5SO_2C_2F_5$ initiation is a good choice on account of the very high productivities it affords at 400° C. For the polymerization of HFP/TFE/PMVE, however, where PMVE chain transfer is of prime concern, $NF_3$ which retains good efficiency at 250° C., is an excellent choice for initiator.

Suitable free radical initiators include $NF_3$, $R_fNF_2$, $R_{f2}NF$, $R_{f3}N$, $R^1N=NR^1$, $R_fOOR_f$, perfluoropiperazine, and hindered perfluorocarbons of the formula $C_nF_{2n+2}$ such as are described in World Patent Application 88/08007, wherein each $R_f$ is independently perfluoroalkyl, preferably containing 1 to 20 carbon atoms, hindered perfluoroalkenes of the formula $C_nF_{2n}$, perfluoro(dialkylsulfones) of the formula $R^1SO_2R^1$, perfluoroalkyl iodides of the formula $R^1I$, perfluoroalkylene diiodides of the formula IRI where the two iodides are not vicinal or geminal, perfluoro (dialkyldisulfides) $R^1SSR^1$, and perfluoroalkyl compounds containing nitrogen-sulfur bonds of the formula $R^1_2NSR^1$, wherein each $R^1$ is independently saturated perfluorohydrocarbyl optionally containing one or more ether groups, isolated iodine, bromine or chlorine substituents, or perfluoroamino groups. By "saturated perfluorohydrocarbyl" is meant a univalent radical containing only carbon and fluorine and no unsaturated carbon-carbon bonds. By an "isolated" iodine, bromine or chlorine substituent is meant that there are no other iodine, chlorine of bromine atoms on carbon atoms alpha or beta to the carbon atom bonded to the the isolated iodine, bromine or chlorine atom. All of these intitators are illustrated in one or more of the Examples. Some of these initiators may only be active at the higher end of the temperature range of the polymerization process. This too is illustrated in the Examples, and the activity of any particular initiator molecule may be readily determined by minimal experimentation. Preferred initiators are $NF_3R_{f2}NF$, $R_fNF_2$, perfluoropiperazine, perfluoro(dialkylsulfones), i.e. $R^1SO_2R^1$, and hindered perfluorocarbons. $NF_3$ is an especially preferred initiator. If higher molecular weight polymers are desired, the initiator should preferably not have any groups present in its structure that cause any substantial chain transfer or termination during the polymerization. Such groups usually include, for instance, organic bromides or iodides or carbon-hydrogen bonds.

The amount of free radical initiator used will vary depending on process conditions. Generally speaking an effective amount is used, an effective amount being that which causes more polymerization to take place with the initiator than without. It is likely that any polymerization without deliberately added initiator present is due to adventitious impurities which can act as initiators at the high polymerization temperatures. Effort should be made to minimize these impurities, such as oxygen. A useful range of initiator concentration has been found to be about 0.003 to about 0.5 g of initiator/kg monomer, preferably about 0.1 to about 0.3 g/kg. Higher or lower amounts are also useful depending upon the initiator, the monomers, goal molecular weights, process equipment, and process conditions used, and can readily be determined by experimentation. The initiator may be added to the reactor as a solution in the monomer(s).

While "solvents" may be added to the polymerization so that the polymerization is carried out in solution or slurry, it is preferred if little or no solvent is added. The polymer formed is soluble in the supercritical HFP under the process conditions. The polymer may be isolated simply by reducing the pressure below about 34 MPa (~5,000 psi), at which point the polymer becomes insoluble. The polymer may also be isolated as fibers or fibrils by flash spinning from solvent and by direct flash spinning of the polymerization mixture. Small amounts of solvents may be used for convenience, as for a carrier for the initiator. FC-75, perfluoro(2-n-butyltetrahydrofuran), and the cyclic dimer of HFP are examples of useful solvents. Another useful solvent is supercritical $CO_2$.

The polymer produced by the instant process is amorphous. Whether this type of a polymer would be amorphous depends on the composition (relative amounts of HFP and TFE), and the distribution of the two repeat units in the polymer. The polymer product should contain at least about 30 mole percent of (I) and at least 1 mole percent of (II), preferably at least 30 mole percent of (II), more preferably about 35 to about 50 mole percent of (I) and about 50 to about 65 mole percent of (II) when a dipolymer is made [no repeat unit (III) present]. Optionally up to about 10 mole percent of repeat unit (III) may be present. When (III) is present a preferred composition is about 35 to about 65 mole percent (I), about 35 to about 65 mole percent (II), and about 0.1 to about 10 mole percent of (III). Various comonomers (III) may be used in the polymerization process, and be incorporated into the polymer. Perfluoro(alkyl vinyl ethers) and perfluorinated terminal alkenes, each optionally substituted with ether, cyano, halo (other than fluorine), sulfonyl halide, hydrogen or ester groups may be used. Also unfluorinated or partially fluorinated olefins or vinyl ethers, optionally substituted as above, may also be used. Useful comonomers include $CF_2=CFOCF_2CF(CF_3)OCF_2CF_2SO_2F$, ethylene, vinylidene fluoride, $CH_2=CHO(C=O)CF_3$, methyl vinyl ether, $CFCl=CF_2$, $CH_2=CFCF_3$, $CH_2=CHCF_3$, $CH_2=CHCF_2CF_2CF_2CF_3$, $CH_2=CHCF_2CF_2Br$, $CF_2=CFCF_2CN$, and $CF_2=CFCF_2OCF_2CF_2SO_2F$.

As mentioned above, the properties of the polymer will be affected not only by the overall composition of the polymer, but by the distribution of the various monomer units in the polymer. The instant process yields a polymer in which the monomer units are more uniformly distributed in the polymer, which gives polymer with more consistent properties. One measure of polymer uniformity is randomness of the monomer units in the polymer. A measure of this is relative amounts of isolated repeat units, diads, triads etc. By diads and triads are meant instances in which two or three repeat units from the same monomer, respectively, occur in the polymer.

Many of the polymers made by the process described herein have relatively small amounts of triads of repeat unit (I), which of course derived from HFP. Thus in such polymers less than 20 mole percent of (I) is in the form of triads, and preferably less than about 15% and more preferably less than about 10%. As would be expected, in polymers with higher amounts of (I), there is a tendency towards higher triad content. The amount of triads in the polymer can be determined by $^{19}F$ NMR (see below for procedure). See the summary of triad data for polymers prepared in Examples 23 and 33–36 in the table following Examples 45 to 49. See Examples 23 and 33–36 and Comparative Example 1 for triad amounts in various polymers.

The instant polymers also have a narrower molecular weight distribution (MWD) than prior art polymers. BY MWD is meant the weight average molecular weight divided by the number average molecular weight (Mw/Mn). Polymers described herein often have MWD's of less than 5, preferably less than 4. Such polymers often have a better combination of processability and physical properties.

Repeat unit (III) may be present to help suppress crystallization and/or lower a glass transition temperature, or for other purposes, and are derived from the corresponding α-perfluoroolefin, perfluorocycloolefin or perfluoro(alkyl vinyl ether). Preferred monomers for unit (III) in which $—C_nF_{2n+1}$ is present are those in which $—C_nF_{2n+1}$ is perfluoro-n-alkyl. When X is $—C_nF_{2n+1}$ it is preferred if n is 2 to 14, while if X is $—OC_nF_{2n+1}$ it is preferred if n is 1 to 4, more preferably 1 or 3.

Since TFE is considerably more reactive in the polymerization than HFP, an excess of HFP is needed to achieve the desired polymer composition. Typically this also means that at the end of the polymerization, much or all of the TFE will have polymerized, but there will be (a considerable amount of) unpolymerized HFP. In a sense this is an advantage, since the HFP can act to help carry the polymer from the reactor, and no additional carrier (such as a solvent) is needed. Typically the TFE will be about 1 to 15 mole percent of the total amount of monomer being fed to the process, with the HFP and other monomer(s) (if present) being the remainder.

The average residence time is the average amount of time any of the material fed to the reactor actually spends in the reactor, and is a function of the volume of the reactor and the volumetric flow of the process ingredients through the reactor. A preferred residence time is about 20 sec to about 10 min, more preferably about 30 sec to about 5 min, especially preferably about 40 sec to about 2 min. A minimum preferred residence time is about 10 sec., more preferably about 15 sec. A maximum preferred residence time is 10 min.

When the process fluids are being added to the reactor, it is preferred if they are preheated just before they enter the reaction to a temperature somewhat less than that of the actual reactor temperature, about 20° C. to about 100° C. less. This allows one to maintain a uniform constant temperature in the reactor itself, and for the newly added materials to start the polymerization reaction immediately upon entry to the reactor.

The amorphous polymers described herein are useful in a variety applications, many of which are related to the fact that the polymers are readily soluble in certain halogenated, especially perfluorinated solvents, and so the polymers are readily useable as films, coatings and encapsulants. Useful solvents include "dimer", perfluorobenzene, perfluoro(n-butyltetrahydrofuran), and FC-10 (tradename of "dimer" 3M fluorocarbon fluid).

Since the polymers are relatively chemically resistant, they may be used to encapsulate articles which must be protected from contamination, corrosion and/or unwanted adhesion to other materials. Films and coatings may be particularly useful because of the inherent properties of the polymer, such as, lack of crystallinity (polymer is clear), low surface energy (and hence poor wetting by water or most organic liquids), low dielectric constant, low index of refraction, low coefficient of friction, low adhesion to other materials, etc.

In the Examples, the $^{19}F$ NMR, which is used to determine the HFP distribution in the polymer, was measured on Broker AC 250 NMR operating at 235 MHz. Polymer samples were loaded in 5 mm NMR tubes and heated to 250° to 360° C. in a narrow bore probe. In the melt, the methine CF's of the HFP units appear at −183.5 ppm if present as isolated units, at −179.5 if present as head to tail diads, and at −177 ppm if present as head to tail triads. It is uncertain whether or not the integration for the HFP triads at −177 ppm also includes higher (than triads) oligomeric blocks. The amount of HFP triads was determined from the ratio of the areas of the $^{19}F$ NMR signal at −177 ppm to the total areas of the signals at −177, −179.5 and −183.5 ppm.

In the Examples, pressure change was used to calculate the weight of tetrafluoroethylene (TFE) added to the mixing reservoir (2). For the tetrafluoroethylene calculations in Examples 1–13, 50, 51 and 65, gauge pressure of TFE (psig) was incorrectly assumed to be absolute pressure (psia). Based upon this incorrect assumption the quantity 160 g of TFE was shown for Examples Examples 1–13, 50, 51 and 65. The actual TFE added in these Examples was about 217 g to 228 grams. The actual amounts of TFE that were added are shown and labeled as such in parenthesis in Examples 1 and 50, 51 and 65. The table on page 12 showing Examples 1–13 reflects the actual TFE measured.

In the Examples, the following abbreviations are used:

8CNVE—perfluoro(8-cyano-5-methyl-3,6-dioxa-1-octene)

Conv.—conversion

GPC—gel permeation chromatography

HFP—hexafluoropropylene

I.D.—inside diameter
IR—infrared (spectrum)
Mn—number average molecular weight
Mw—weight average molecular weight
Mv—viscosity average molecular weight
O.D.—outer diameter
PMVE—perfluoro(methyl vinyl ether)
TFE—tetrafluoroethylene
In the Examples, the following materials are used:
"dimer"—a perfluorinated solvent which is d in U.S. Pat. No. 5,237,049
FC-40—Fluorinert electronic liquid sold by 3M Industrial Chemicals Division, thought to be substantially perfluoro(tributylamine).
FC®-75—Fluorinert® Electronic Liquid, sold by 3M Industrial Chemicals Products Division, thought to be substantially perfluoro(2-butyltetrahydrofuran)
Kalrez® Perfluoroelastomer Parts—a tetrafluoroethylene/ perfluoro(methyl vinyl ether) and curesite monomer copolymer part available from E. I. du Pont de Nemours and Company, Inc., Wilmington, Del., USA
Kapton® Polyimide Film—a polyimide film available from E. I. du Pont de Nemours and Company, Inc., Wilmington, Del., USA
Mylar® Polyester Film—a poly(ethylene terephthalate) film available from E. I. du Pont de Nemours and Company, Inc., Wilmington, Del., USA
Nordel® Hydrocarbon Rubber—an EPDM elastomer available from E. I. du Pont de Nemours and Company, Inc., Wilmington, Del., USA
PET poly(ethylene terephthalate)
Viton® Fluoroelastomer—a copolymer of vinylidene fluoride and hexafluoropropylene available from E. I. du Pont de Nemours and Company, Inc., Wilmington, Del., USA

BRIEF DESCRIPTION OF THE DRAWING

In FIG. 1, within the barricade $NF_3$, initiator is loaded into loop (1) and then blown to reservoir (2) using hexafluoropropylene (HFP). In (2) tetrafluoroethylene is added to the HFP/$NF_3$ mixture, and the total mixture in (2) is then removed from the bottom of (2), boosted to a higher pressure and recirculated through the Monomer Recycle Loop, and then part of it is sent to the heated (polymerization) reactor (5) and part of it is recycled through valve (4) back to (2) after the pressure is lowered at pressure regulator (3) to the pressure of the contents of (2). After exiting reactor (5), the pressure of the mixture is reduced (often to atmospheric pressure) at back pressure regulator (6) and the copolymer product is isolated in glass collection bottle (7). Gaseous matter leaving the collection bottle is passed through meter (8) which is used to measure the amount of unreacted gaseous monomers. A more detailed description of the use of the apparatus of FIG. 1 appears below.

EXAMPLE 1

Figure 1:
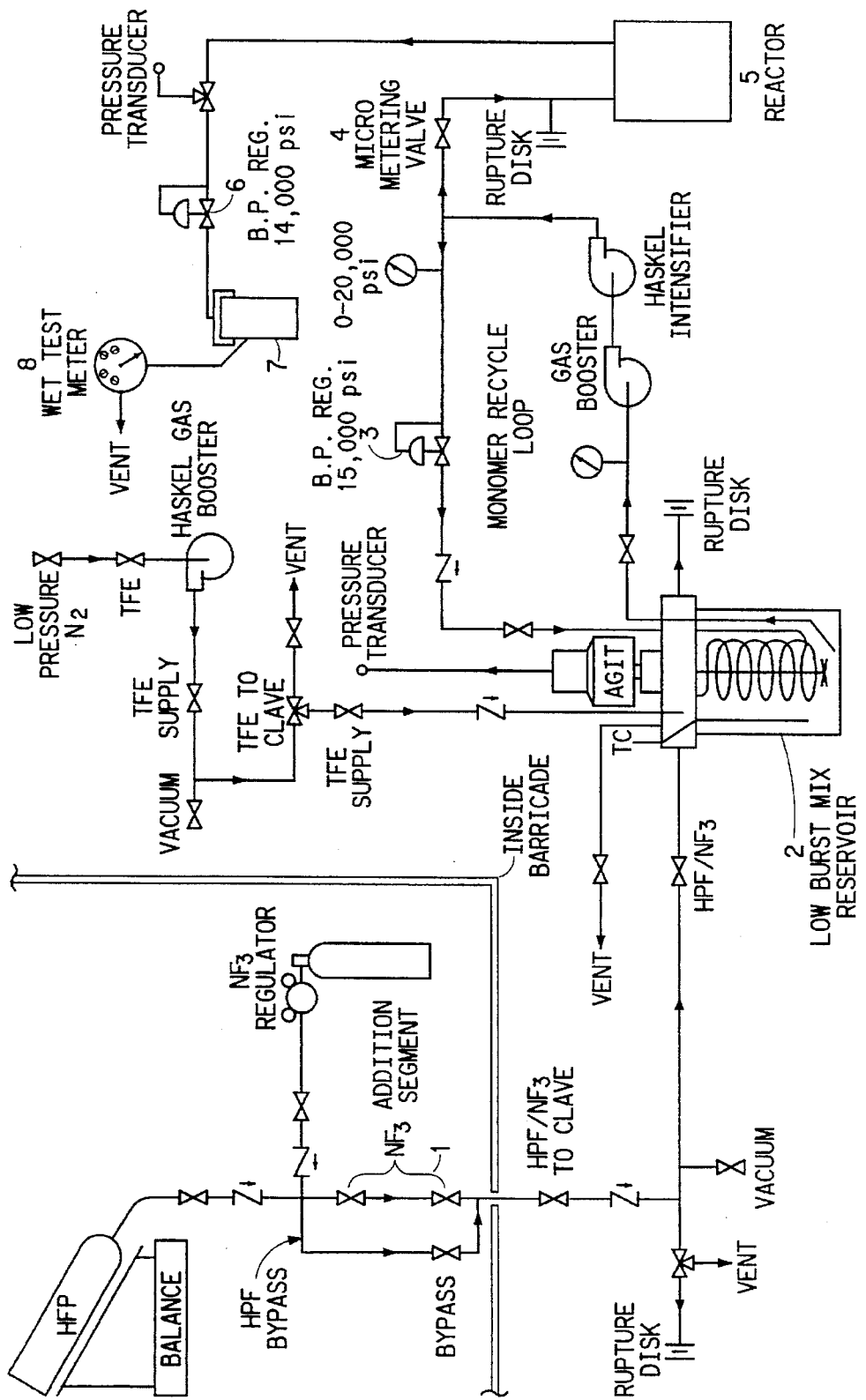
FIG. 1 is a schematic diagram of a High Pressure Continuous Unit which can be used for the continuous polymerization described herein.

Continuous Polymerization in 10 ml Autoclave with Agitation

All the reactants needed for a single run were premixed in a reservoir, pressured to 103 MPa, bled off through a heated pressure vessel at slightly lower pressure, and finally vented to atmospheric pressure in the form of solid polymer foamed with unreacted monomer. The detailed procedure given below for Example 1 is in reference to the reactor schematic, FIG. 1.

Preparation of Homogeneous Monomer/Initiator Mix

A 25 ml loop (1) off the feed line to a 3.8 L reservoir (2) was pressured to 710 kPa with nitrogen trifluoride at ambient temperature (~0.6 g of $NF_3$). The 3.8 L reservoir was then loaded with 160 g of TFE (actual TFE loaded was 222 g) and 4000 g of HFP, a portion of the HFP being used to blow the $NF_3$ into the reservoir (2). Liquid monomer phase was pulled off the bottom of the reservoir, pressured to 103 MPa, and then recirculated back to the reservoir via back pressure regulator (3). The run was not started until the contents of the clave had been mixed by 10 minutes of such recirculation. Recirculation through the reservoir was maintained for the duration of the run. No effort was made to control the temperature of the reservoir which varied in the case of this run from 23° C. at the start to 33° C. at the finish.

Monomer Feed to Reactor

Flow was maintained through the system by letting monomer pressure down in stages, from 103 MPa in the recirculation loop to 96.5 MPa in the reactor and finally to atmospheric pressure in the product collector. The rate of flow was controlled by a micrometering valve (4) in the stainless steel line that connected the reservoir recirculation loop at 103 MPa with the reactor at 96.5 MPa. Reactor pressure was maintained at 96.5 MPa by back pressure regulator (6) placed after reactor (5). Micrometering valve (4) was opened until monomer flowed through the reactor at 10 to 12 g per minute, the measurement of flow rates being discussed later. In order to maintain steady flow throughout the run, periodic adjustments were made to micrometering valve (4).

Reactor

As already mentioned, a flexible stainless steel tube, 0.40 cm O.D. by 0.16 cm I.D., was run from micrometering valve (4) to the front end of reactor (5). In an effort to bring the monomers up to reactor temperature rapidly, the last ~61 cm of tubing before the reactor was wrapped with electrical tape and preheated to ~200° C. Considering that the internal volume of this preheated segment is small relative to the reactor proper (~1 ml in the preheated line vs. 10 ml in the reactor) and that reaction rates are slower at 200° C. than at 275° C., polymer formation in the preheated line was ignored for the purposes of productivity calculations. Reactor (5), in this Example a 10 cc stainless steel autoclave (5.2 cm long×1.1 cm I.D. and containing two loose 0.63 cm stainless steel balls), was rocked vigorously with a paint shaker while heating to 275° C.

Product Isolation

A piece of flexible stainless steel tubing was run from reactor (5) to back pressure regulator (6) at which point pressure was dropped from 96.5 MPa to atmospheric. In spite of the fact that no effort was made to warm either the line or the valve, no plugging was observed in this and the majority of runs. When plugging did occur, it was most often at the low pressure side of the regulator (6) where foamed polymer was left when the monomer flashed off. To minimize plugging, the low pressure side of the let down valve was drilled out to provide as large an orifice as possible and then connected directly to a several liter glass collection bottle (7). Gaseous monomer exiting the glass collection bottle was passed through wet test meter (8), the liters of monomer per minute being converted to monomer flow in grams per minute. An average flow rate of 10.9 g/min was thus observed over the 247 minute duration of this run. Given that the density of HFP at 275° C./96.5 MPa is ~1.29 g/ml, the average residence time for the monomers in reactor (5) was ~1.2 minutes. Polymer was recovered from the glass collection bottle (7) as large chunks of foamed white solid weighing 170.2 g. Pulling residual monomer off with a vacuum pump reduced the weight of polymer to 159 g for a productivity of 3.8 kg/L/hr. Fluorine NMR of the polymer melt at 330° C. found 43 mole % (53 wt %) HFP copolymerized with 57 mole % (47 wt %) TFE, allowing the calculation of 54% TFE conversion per pass and 3.2% HFP conversion per pass. Rolling 1.5 g of this polymer with 5 ml of FC-75 at room temperature gave a viscous solution. Transparent films were pressed at 160° C. by applying 8000 lbs of pressure for 1 minute to 1 g samples held between Kapton® polyimide film cover sheets. Under an applied weight of 15 kg, a 2 g sample extruded through a melt indexer at 0.63 g/minute at 200° C. GPC in FC-75 solvent showed Mw=235,000 and Mn=94,700 for a Mw/Mn=2.87.

Characterization Summary

The results of Example 1 as well as of Examples 2 to 13 made under the same conditions are tabulated below. Reproducibility was excellent considering that the process has yet to be automated.

| Ex. | Residence Time | Polymer Wt % HFP[1] | Melt Index[2] | Conv. Per Pass HFP | Conv. Per Pass TFE | kg/L/hr | Mw/Mn[3] | $N_{inh}$[4] |
|---|---|---|---|---|---|---|---|---|
| 1 | 1.2 min | 53% | 0.6 g/min | 3.2% | 54% | 3.8 | 2.87 | 0.39 |
| 2 | 0.9 min | 45% | 0.4 g/min | 2.4% | 54% | 4.2 | 3.65 | 0.45 |
| 3 | 1.0 min | 50% | 0.3 g/min | 2.6% | 50% | 3.9 | 3.53 | 0.54 |
| 4 | 0.9 min | 49% | 0.5 g/min | 2.2% | 45% | 3.7 | 3.63 | 0.49 |
| 5 | 1.0 min | 51% | 0.4 g/min | 2.5% | 46% | 3.8 | 3.23 | 0.49 |
| 6 | 1.0 min | 51% | 0.6 g/min | 2.7% | 50% | 3.9 | 3.34 | 0.51 |
| 7 | 1.0 min | 51% | 1.3 g/min | 2.6% | 47% | 3.8 | 3.12 | 0.41 |
| 8 | 1.0 min | 50% | 0.7 g/min | 2.5% | 48% | 3.6 | 2.99 | 0.44 |
| 9 | 1.0 min | 54% | 1.0 g/min | 2.7% | 44% | 3.6 | 3.83 | 0.29 |
| 10 | 1.1 min | 53% | 0.7 g/min | 3.1% | 52% | 3.8 | 2.85 | 0.41 |
| 11 | 1.2 min | 50% | 0.8 g/min | 3.1% | 55% | 3.7 | 2.62 | 0.39 |
| 12 | 1.1 min | 53% | 0.7 g/min | 2.8% | 47% | 3.5 | 2.45 | 0.48 |
| 13 | 1.2 min | 53% | 1.0 g/min | 3.1% | 53% | 3.6 | 2.57 | 0.41 |

[1]Composition determined by fluorine NMR in the melt at 300–340° C.
[2]Melt index determined at 200° C. with a 15 kg weight
[3]Mw and Mn determined by GPC using FC-75 solutions, versus linear poly(hexafluoropropylene oxide) standards, one with Mn ~20,000, the other with Mn ~70,000
[4]Inherent viscosity in FC-75

COMPARATIVE EXAMPLE 1

An 85 ml autoclave was loaded with 60 ml of perfluorodimethylcyclobutane and 0.25 g of cobalt trifluoride. The autoclave was sealed, chilled, and evacuated. Hexafluoropropylene was used to sweep in 4.25 g of TFE. Enough HFP was added to bring the pressure of the autoclave to 930 MPa at 23° C. (~30 g of HFP). The autoclave was heated to 199° C. and 296 MPa, an additional 6.9 MPa of HFP being added to match Eleuterio's condition of 303 MPa. The autoclave was held at ~200° C. for four hours and then cooled and vented. The resulting polymer solution was filtered to get rid of pink residues (presumably containing insoluble cobalt compounds), stripped to heavy oil on a rotary evaporator and then blown down to 0.94 g of solid using a stream of nitrogen. This solid has an inherent viscosity of 0.207 in FC-75 closely matching Eleuterio's Example II. Mw/Mn was 6.39, a very broad molecular weight distribution compared to polymers made by our process. In a TGA analysis, this polymer had lost 20% of its weight by 340° C.

| Ex. | Residence Time | Polymer Wt % HFP | Melt Index | Conv. Per Pass HFP | Conv. Per Pass TFE | kg/L/hr | Mw/Mn |
|---|---|---|---|---|---|---|---|
| Com. 1 | 240 min | 57% | — | — | — | 0.02 | 6.39 |

EXAMPLES 14 TO 19

Continuous Polymerization in 10 mL Autoclave, With and Without Agitation

The same set up was used as in Examples 1 to 13. About 80 to 90 grams TFE, 200 g HFP and 0.6 g NF3 were loaded to the mixing clave, making the ratio of initiator relative to monomer about twice as great as in Examples 1 to 13, and reactor temperature was 300° to 325° C. instead of 275° C., In all Examples but 14 the reactor was agitated by vigorous rocking. Product characterizations are shown below.

| Ex. | Residence Time | Polymer Wt % HFP[1] | Melt Index[2] | Conv. Per Pass HFP | Conv. Per Pass TFE | kg/L/hr | Mw/Mn[3] |
|---|---|---|---|---|---|---|---|
| NO SHAKING, 300° C. | | | | | | | |
| 14 | 0.9 min | 51% | 2 g/min | 2.7% | 64% | 3.9 | 3.57 |
| SHAKING, 300° C. | | | | | | | |
| 15 | 0.5 min | 46% | 20 g/min | 1.2% | 36% | 4.0 | 2.79 |
| 16 | 0.7 min | 56% | 2 g/min | 2.7% | 52% | 4.4 | 2.12 |
| 17 | 0.9 min | 55% | 20 g/min | 4.1% | 84% | 5.5 | 3.60 |
| 18 | 1.9 min | 60% | 20 g/min | 5.4% | 91% | 3.2 | 2.41 |
| SHAKING, 325° C. | | | | | | | |
| 19 | 0.9 min | 60% | 4 g/min | 5.3% | 86% | 6.4 | 2.38 |

[1]Composition determined by fluorine NMR in the melt at 300–340° C.
[2]Ex. #14 melt index at 200° C. with 15 kg weight
Ex. #15 melt index at 200° C. with 15 kg weight
EX. #16 melt index at 200° C. with 15 kg weight
Ex. #17 melt index at 200° C. with 15 kg weight
Ex. #18 melt index at 200° C. with 15 kg weight
Ex. #19 melt index at 200° C. with 5 kg weight
[3]Mw and Mn determined by GPC using FC-75 solutions, versus linear poly(hexafluoropropylene oxide) standards, one with Mn ~20,000, the other with Mn ~70,000

EXAMPLES 20 TO 44

Continuous Polymerization in Tube, No Agitation

The same set up was used as for Examples 1 to 13, except that in these Examples reactor (5) was a 0.95 cm OD×0.52 cm ID×5.3 m long coil of stainless steel tubing with an internal volume of ~110 ml. The reactor coil was heated using a sand bath. In view of the 5.3 m length the tube no preheater was needed. Results for Examples 20 to 44 are shown in the table below. Example 43 was unique in that 435 ml of liquid FC-75 was added along with the initial monomer charge. The result of doing this is that the product was obtained as ~400 ml of solution containing 0.16 g of dissolved polymer/ml.

| Ex. | °C. | MPa | Res Time | Weight % HPP Feed | Polymer[1] | % Conversion HFP | TFE | kg/L/hr |
|---|---|---|---|---|---|---|---|---|
| ~CONSTANT T, P, AND FEED |
| 20 | 250° C. | 75.8 | 21 min. | 98% | 64% | 2.9 | 81 | 0.2 |
| 21 | 250° C. | 75.8 | 9 min. | 98% | 61% | 2.2 | 72 | 0.3 |
| 22 | 250° C. | 75.8 | 5 min. | 98% | 59% | 2.2 | 76 | 0.5 |
| 23 | 250° C. | 75.8 | 4 min. | 98% | 58% | 1.5 | 55 | 0.7 |
| 24 | 250° C. | 75.8 | 3 min. | 98% | 58% | 1.3 | 37 | 0.6 |
| CONSTANT T, P, AND ~TIME |
| 25 | 250° C. | 96.5 | 6 min. | 98% | 58% | 2.3 | 84 | 0.6 |
| 26 | 250° C. | 96.5 | 6 min. | 96% | 53% | 3.8 | 84 | 0.9 |
| 27 | 250° C. | 96.5 | 6 min. | 96% | 54% | 3.4 | 72 | 0.9 |
| 28 | 250° C. | 96.5 | 6 min. | 96% | 52% | 3.2 | 74 | 0.9 |
| 29 | 250° C. | 96.5 | 6 min. | 96% | 53% | 3.8 | 86 | 1.0 |
| 30 | 250° C. | 96.5 | 6 min. | 95% | 50% | 4.3 | 80 | 1.1 |
| 31 | 250° C. | 96.5 | 6 min. | 94% | 44% | 2.9 | 56 | 0.8[2] |
| 32 | 250° C. | 96.5 | 8 min. | 92% | 47% | 4.6 | 63 | 0.9[2] |
| CONSTANT P, FEED, AND ~TIME |
| 33 | 275° C. | 75.8 | 18 min. | 98% | 67% | 3.3 | 85 | 0.2 |
| 34 | 250° C. | 75.8 | 21 min. | 98% | 64% | 2.9 | 81 | 0.2 |
| 35 | 225° C. | 75.8 | 21 min. | 98% | 57% | 1.7 | 65 | 0.1 |
| 36 | 325° C. | 96.5 | 6 min. | 96% | 59% | 5.1 | 89 | 1.1 |
| 37 | 300° C. | 96.5 | 5 min. | 96% | 56% | 5.4 | ~100 | 1.4 |
| 38 | 275° C. | 96.5 | 7 min. | 96% | 59% | 5.2 | 90 | 1.0 |
| 39 | 250° C. | 96.5 | 6 min. | 96% | 53% | 3.8 | 84 | 0.9 |
| CONSTANT T, FEED, AND ~TIME |
| 40 | 250° C. | 62.0 | 5 min. | 98% | 59% | 1.9 | 65 | 0.5 |
| 41 | 250° C. | 75.8 | 5 min. | 98% | 59% | 2.2 | 76 | 0.5 |
| 42 | 250° C. | 96.5 | 6 min. | 98% | 60% | 2.3 | 75 | 0.6 |
| IN THE PRESENCE OF FC-75 SOLVENT AND THIRD MONOMER, 8CNVE |
| 43 | 250° C. | 96.5 | ~6 min. | 90+%[3] | 64%[3] | 2.3 | 31 | 0.4 |
| IN THE PRESENCE OF THIRD MONOMER, PMVE |
| 44 | 250° C. | 96.5 | ~6 min | 94%[4] | 47%[4] | 3.1 | ~100 | 0.9 |

[1]Composition determined by fluorine NMR in the melt at 300–340° C.
[2]Incomplete removal of polymer from reactor, kg/L/hr probably larger than reported
[3]Several percent 8CNVE, CF$_2$=CFOCF$_2$CF(CF$_3$)OCF$_2$CF$_2$CN in feed. Polymer composition by fluorine NMR. 63.8 wt % HFP, 34.1 wt % TFE, 2.1 wt % 8CNVE
[4]Starting mix: 94.3% wt % HFP, 3.8 wt % TFE, 1.9 wt % PMVE
Polymer: 37.2 mole % HFP, 60.7 mole % TFE, 2.1 mole % PMVE Molecular weight distributions were measured for only a few of the samples made in the tubular reactor. Distributions appear to be a bit broader and less uniform than experienced in the shaken autoclave (Examples 1–13 and 15–19) or the well-stirred reactor (Example 85).

| Example | Mw/Mn |
|---|---|
| 38 | 4.96 |
| 27 | 3.20 avg. of 2 |
| 28 | 3.93 avg. of 2 |
| 29 | 3.48 avg. of 2 |

EXAMPLES 45 TO 49

Continuous Polymerization in Tube, No Agitation Effect of Decreasing Initiator

The same tubular reactor as described in Examples 20 to 44 was run at 250° C./96.5 MPa with a residence time of 5.6 to 6.0 minutes and 2500 g HFP+50 g TFE+a variable amount of NF$_3$ added to the 3.8 L mixing reservoir. The effects of varying the amount of NF$_3$ in the starting monomer mix is shown below.

| Ex. | Estimated Grams NF$_3$ in Feed[1] | Wt % HFP Feed | Polymer | % Conversion HFP | TFE | Kg/L/hr |
|---|---|---|---|---|---|---|
| 45 | 0.7 g | 98% | 58% | 2.3 | 84 | 0.6 |
| 46 | 0.4 g | 98% | 58% | 1.6 | 56 | 0.4 |
| 47 | 0.2 g | 98% | 60% | 1.9 | 62 | 0.4 |
| 48 | 0.1 g | 98% | 58% | 1.5 | 54 | 0.3 |
| 49 | None | 98% | 57% | 0.7 | 28 | 0.2 |

[1]The grams of NF$_3$ added to the monomer mixing reservoir were estimated from PV = nRT. The amount of NF$_3$ delivered to the reactor for polymerization, however, may be quite a bit less if the highly volatile NF$_3$ concentrates in the vapor phase rather than in the liquid monomer phase that is pumped to the reactor.

Initiation in the absence of NF$_3$ is probably the result of adventitious oxygen. Shown immediately below are the results of 19F NMR analyses giving the percentages of HFP repeat units which are isolated, in diads and in triads for certain Examples.

| Example # | Wt. % HFP | % of Total CF's Found in Polymer by $^{19}$F NMR | | |
|---|---|---|---|---|
| | | Triads | Diads | Isolated |
| 34 | 67% | 12.40 | 41.47 | 46.13 |
| 35 | 64% | 15.86 | 39.42 | 44.72 |
| 23 | 59% | 9.06 | 36.72 | 54.22 |
| 36 | 57% | 9.92 | 35.59 | 54.49 |
| 33 | 47% | 5.56 | 25.53 | 68.91 |
| Comparative Example #1 | 57% | 26.63 | 27.26 | 46.4 |

EXAMPLE 50

The agitated reactor was set up as in Example 1. Instead, however, of using NF$_3$ as the initiator, a solution of 0.8 ml of perfluorodibutylamine [(C$_4$F$_9$)$_2$NF] dissolved in 5 ml of HFP cyclic dimer (perfluorodimethylcyclobutane) was introduced directly in the 1 gallon reservoir 2 prior to the start of the run. A mix of this initiator with 160 g of TFE (actual TFE loaded was 223 g) and 4000 g of HFP was run through the 10 ml agitated reactor at ~12 g/min at 275° C. (estimated residence time 1 minute) and 96.5 MPa for 315 minutes. This gave 146 g of poly(HFP/TFE), for a productivity of 2.8 kg/L/hr. The polymer was soluble in FC-75 and found to have Mw=603,000, Mn=226,000, and Mv=546,000. Fluorine NMR in the melt at 340° C. found 49 wt % HFP, 51 wt % TFE, and 74% of the methine FC's as triads. Conversion per pass was 38% for TFE and 1.9% for HFP.

EXAMPLES 51–55

The agitated reactor was set up as in Example 1. Instead, however, of using NF$_3$ as the initiator, a solution of 1.5 g of perfluorodibutylamine [(C$_4$F$_9$)$_2$NF] dissolved in 5 ml of HFP cyclic dimer (perfluorodimethylcyclobutane) was introduced directly in the 1 gallon reservoir 2 prior to the start of the run. A mix of the initiator with 160 g of TFE (actual TFE loaded was 222 g) and 4000 g of HFP was run through the 10 ml agitated reactor at 9.5 g/min at 325° C. (estimated residence time 1.2 min) and 96.5 MPa for 365 minutes. This gave 239 g of poly(HFP/TFE), for a productivity of 4.0 kg/L/hr. The polymer was soluble in FC-75. Fluorine NMR in the melt at 320° C. found 54 wt % HFP/46 wt % TFE with 6.1% of the HFP methines as triads. GPC in FC-75 found Mw=348,000, Mn=130,000, Mv=304,000. Inherent viscosity in FC-75 was 0.413. Per pass conversions were 63% for TFE and 3.8% for HFP.

A major difference between $NF_3$ and $(C_4F_9)_2NF$ is that $(C_4F_9)_2NF$ is a relatively nonvolatile liquid. This means that when a mix of HFP, TFE, and $(C_4F_9)_2NF$ is made in mixing reservoir 2, almost all of the $(C_4F_9)_2NF$ will reside in the liquid monomer phase. This in turn allows us to estimate with moderate accuracy how much $(C_4F_9)_2NF$ was actually used as an initiator in this run: when 3472 g out of 4223 g (82%) of starting monomer mix was pumped through reactor 5, a like fraction of the $(C_4F_9)_2NF$, 82% or about 1.23 g, was probably used to initiate polymerization. Knowing that 1.23 g of $(C_4F_9)_2NF$ initiated 239 g of polymer with Mn=130,000 and assuming that there are two $(C_4F_9)_2NF$ derived end groups per chain allows one to calculate that each $(C_4F_9)_2NF$ generated in fact 1.4 radicals. Generating 1.4 radicals out of a potential maximum of 2 [F● and $(C_4F_9)_2N●$] represents an initiator efficiency of 70% for $(C_4F_9)_2NF$ at 325° C. A similar calculation for Example 50 above shows that the efficiency of $(C_4F_9)_2NF$ drops to about 24% at 275° C.

Properties of the $(C_4F_9)_2NF$ initiated polymer made here in Example 51 are compared to those of closely bracketing $NF_3$ initiated runs (Examples 52 to 55) made in the same equipment:

| Ex # | Gel Permeation Chromatography Data | | | | | $^{19}F$ NMR DATA | |
|---|---|---|---|---|---|---|---|
| | Mw × 10⁻³ | Mn × 10⁻³ | Mw/Mn | Mv × 10⁻³ | IV | Wt % HFP | Triads |
| 52 | 334 | 129 | 2.59 | 292 | 0.411 | 53% HFP | 6.5% |
| 51 | 348 | 130 | 2.67 | 304 | 0.413 | 54% HFP | 6.1% |
| 53 | 371 | 142 | 2.99 | 326 | 0.443 | 50% HFP | 5.3% |
| 54 | 423 | 137 | 3.08 | 367 | 0.492 | 51% HFP | 5.0% |
| 55 | 451 | 156 | 2.90 | 397 | 0.517 | 48% HFP | 3.2% |

EXAMPLE 56

The agitated reactor was set up as in Example 1. Instead, however, of using $NF_3$ as the initiator, 11 psig of $CF_3OOCF_3$ (about 0.3 g) was introduced into a 25 ml initiator loop 1. A mix of this initiator with 160 g of TFE (actual TFE loaded was 221 g) and 4000 g of HFP was run through the 10 ml agitated reactor at about 10.6 g/min at 275° C. and 14,000 psi for 340 minutes. This gave 53 g of poly(HFP/TFE), for a productivity of 1.0 kg/L/hr. The polymer was soluble in FC-75 and found to have Mw=852,000 and Mn=235,000.

EXAMPLE 57

A 50 wt % HFP copolymer of HFP and TFE, which had a melt viscosity of 100 sec⁻¹ of 854 Pa·s was dissolved in a variety of solvents to test solubility. To an Erlenmeyer flask fitted with a reflux condenser and magnetic stirrer were added 95 g various solvents and 5 g polymer. The mixtures were heated on a hot plate with stirring until reflux occurred. The solvents tested were "dimer", FC-75, FC-40 and hexafluorobenzene.

The polymer dissolved in all solvents tested to form clear, low viscosity solutions. When cooled to room temperature, all samples remained as clear, low viscosity fluids.

EXAMPLE 58

The FC-75 solution of Example 57 was used to prepare dipped coatings on various metals. Metal coupons of size 2.5 cm×7.6 cm×0.64 mm were cleaned in an ultrasonic bath with acetone, dried at 150° C. for 4 hours, cooled to room temperature and dipped into the 5% solution. Excess solution was drained off. The coupons were dried overnight at 150° C. Metals tested were copper, brass, aluminum, stainless steel, galvanized steel and chrome plated steel. All coatings were smooth and clear. The copper coupon had some discoloration.

Contact angle measurements of a droplet of water on each coating were made. Contact angles were 115°+/−2° advancing and 94°+/−2° receding, showing that the coatings were uniform and were hydrophobic.

Film thickness was measured for each coupon using a Tencor Stylus Profilometer. Film thickness was 1.7 μm+/− 0.5 μm.

Film adhesion was tested using ASTM D3359. Each coated film was scratched in a cross hatch pattern of 10 lines per 2.5 cm using a razor knife edge. Adhesive tape was pressed against the cross hatch scored film. The tape was removed and the film examined. No removal of polymer film from the metal coupon occurred. The cross hatched scored coated films were placed in boiling water for 1 hour. The coupons were removed from the water, dried at 150° C. for 1 hour and were cooled to room temperature. An adhesive tape was again pressed against the cross hatch scored film and then removed. No removal of polymer film from the metal coupon occurred. This shows that the coated films are strongly adhered to the metal coupons and can resist the action of boiling water.

EXAMPLE 59

The FC-75 solution of Example 57 was used to prepare dipped coatings on various polymers. Polymer strips of size 2.5 cm×7.6 cm×1.9 mm were prepared from nylon 6,6, Nordel® vulcanizate, neoprene vulcanizate, Viton® vulcanizate, Kalrez® vulcanizate, and strips of size 2.5 cm.×7.6 cm×0.25 mm were cut from films of Mylar® PET and Kapton® polyimide. All samples were cleaned in an ultrasonic bath with acetone, dried at 150° C. for 4 hours, cooled to room temperature and dipped into the 5% solution. Excess solution was drained off. The coated samples were dried overnight at 150° C. All coatings were smooth and clear.

Contact angle measurements of a droplet of water on each coating were made. Contact angles were 115°+/−4° advancing and 94°+/−4° receding, showing that the coatings were uniform and were hydrophobic.

Film thickness was measured for coatings on nylon, Mylar® and Kapton® using a Tencor Stylus Profilometer. Film thickness was 1.7 μmm +/−0.5 μm.

Film adhesion was tested using ASTM D3359. Each coated film was scratched in a cross hatch pattern of 10 lines per 2.5 cm using a razor knife edge. Adhesive tape was pressed against the cross hatch scored film. The tape was removed and the film examined. No removal of the coated film from the polymer surface occurred. The cross hatch scored coated strips were placed in boiling water for 1 hour. The strips were removed from the water, dried at 150° C. for 1 hour and were cooled to room temperature. An adhesive tape was again pressed against the cross hatch coating and then removed. No removal of coating film from the polymer strips occurred. This shows that the coated film are strongly adhered to the polymer strips and can resist the action of boiling water.

EXAMPLE 60

The solution of Example 57 in FC-75 was used to prepare dipped coatings on various fabrics. Pieces of fabric were cut to size 15.2 cm square. The fabrics were a loose woven nylon, a loose woven PET polyester, a loose woven cotton and a Nomex® felt. The fabrics were dipped into the 5% solution and were squeezed by hand to remove excess solution. The fabrics were dried for 1 hour at 150° C. After drying, all fabrics remained soft and flexible and were porous.

A drop of distilled water was placed on each fabric and on a portion of the same fabric that had not been treated. In each case, the water wet and penetrated the untreated fabric, but formed a spherical drop on the treated fabric and did not penetrate. Thus, the treated fabrics were hydrophobic.

EXAMPLE 61

The solution of Example 57 in FC-75 was treated as a mold release agent. A size 214 O-ring mold was cleaned with "Easy Off" commercial oven cleaning agent. The mold was washed with water and dried by heating in a press at 177° C. for 15 min. The mold had 30 sites for molding O-rings. Fifteen sites were spray coated with solution. The remaining sites were coated with commercial mold release, McLube No. 1725. The coatings were dried by placing the mold in a press at 177° C. for 15 min. Kalrez® O-ring preforms were placed in the proper sites and the mold was placed in a press at 177° C. for 15 min to mold the O-rings.

After the first molding cycle there was some sticking to the McLube coated sites. The solution coated sites had no sticking. The mold cycle was repeated for three additional cycles with no additional mold release coating applied to any of the sites. After the final mlding cycle, about 30% of the O-rings removed from the sites lubricated with McLube were torn during removal from the mold due to sticking. None of the O-rings removed from sites coated with solution were torn. There was no sticking of O-rings at the solution coated sites.

EXAMPLE 62

The solution of Example 57 in FC-75 was tested as a mold release agent. A conventional golf ball compression mold was cleaned with "Easy Off" commercial oven cleaning agent. The mold was washed with water and dried by heating in a press at 204° C. for 15 min. The mold was spray coated with solution and was dried by placing the mold in a press at 204° C. for 4 hours. The mold cavity was filled with a Surlyn® ionomer golf ball cover and a spiral wound rubber core. The golf ball was compression molded for 15 min at 204° C.

When the mold was used without solution coating, the golf ball cover adhered to the metal mold and pulled away from the core when the ball was removed from the mold. When the mold was coated with the solution there was no sticking and the molded golf ball was easily removed.

EXAMPLE 63

A linear low density polyethylene with melt index 1 g/10 min was extruded through a capillary die of size 0.76 mm×2.5 cm×90° using an Instron® capillary rheometer. The shear stress required to extrude the polyethylene at 220° C. at a shear rate of 347 sec$^{-1}$ was 4.0×10$^5$ Pa. The surface of the extrudate was rough and distorted.

To the polyethylene was added TFE/HFP copolymer at a level of 0.1%. The extrusion through the capillary die was repeated. When the polyethylene containing the TFE/HFP copolymer was extruded at 220° at a shear rate of 347 sec$^{-1}$ the shear stress required was reduced to 2.0×10$^5$ Pa, and the extrudate was smooth and was not distorted. Thus, the presence of the copolymer reduced the shear stress required to extrude the polyethylene from 4.0×10$^4$ Pa to 2.0×10$^4$ Pa and the surface of the extrudate became smooth and undistorted. The TFE/HFP copolymer acted as a processing aid for the polyethylene.

EXAMPLE 64

An 0.38 mm×9.5 mm×90° tungsten carbide capillary was coated with a 1% solution of TFE/HFP copolymer dissolved in FC-75. The coating was dried at 250° C. for 2 hours. A linear low density polyethylene, GRSN 7047 from Union Carbide, melt index 1 g/10 min, containing 2.5% colloidal silica (to act as an abrasive material) was extruded through the capillary die using an Instron capillary rheometer at a temperature of 220° C. and at a shear rate of 833 sec$^{-1}$.

When the polyethylene was extruded through the capillary die with no solution coating on the capillary, at a temperature of 220° C. and at a shear rate of 833 sec$^{-1}$ the shear stress required was 4.5×10$^5$ Pa. The surface of the extrudate was rough and distorted. When the polyethylene was extruded through the coated capillary under the same conditions, the shear stress required dropped to 2.5×10$^5$ Pa shortly after start up and the surface of the extrudate was smooth and undistorted. The shear stress slowly rose, over a period of about 2 hours to 4.5×10$^5$ Pa, as the solution coating was slowly worn away by the abrasive polyethylene. When the shear stress reached a level greater than 3.0×10$^5$ Pa the surface of the extrudate again became rough. This example shows that the solution coating on the capillary acted as an extrusion aid that significantly reduced shear stress and eliminated surface roughness. When the coating was completely worn away, after two hours, the shear stress returned to the uncoated value and surface roughness reappeared.

EXAMPLE 65

Polymerization in Presence of $CO_2$

The agitated reactor was set up as in Example 1, loading a mixture of 3000 g of HFP, 160 g of TFE (actual: 226), 157 g of $CO_2$ diluent, and 1.5 g of $NF_3$. This mixture was run through the 10 cc agitated reactor at about 10 to 11 g/min at 300° C. and 96.5 MPa for 278 minutes. This gave 254 g of polymer for a productivity of 5.5 kg/L/hr. The polymer had an inherent viscosity of 0.254 and a melt flow of 4 g/min at 200° C. under a load of 5 kg in a melt indexer.

EXAMPLES 66–84

Polymerizations in Examples 66 to 84 here were run in a semicontinuous fashion using the equipment and general methods described in Example 1. Initiator performance is compared in terms of grams or polymer made per gram of initiator. For this is used the formula: (grams of polymer)÷ [(grams of initiator added to the mixing clave)×(fraction of reaction mixture run through the polymerizer)]. Polymerization temperatures were measured using a thermocouple placed between the wall of the reactor and its heating jacket except in Example 85 in which case reactor temperature was measured internally. Example 85 also changes the reactor from a shaken tube to a larger, mechanically well-stirred vessel with separately metered flows for the HFP, the TFE, and a HFP/$NF_3$ mixture. The larger scale and the use of calibrated flow meters in Example 85, should make monomer feed ratios more accurate.

EXAMPLE 66

$CF_3CF_2CF_2C(CF_3)_2NF_2$ Initiation

The 10 cc shaken autoclave was set up as in Example 1. Instead of using $NF_3$ as initiator, a solution of 0.5 ml $CF_3CF_2CF_2C(CF_3)_2NF_2$ dissolved in 2.0 ml of HFP cyclic dimer (perfluorodimethylcyclobutane) was introduced to 1 gallon reservoir 2 prior to the start of the run. A mix of this initiator with 114 g of TFE and 2000 g of HFP was run through the 10 ml agitated reactor at 11 g/min at 275° C. (estimated residence time 1.2 min) and 96.5 MPa (14,000 psi) for 154 minutes. After vacuum pump drying at room temperature, this gave 51.1 g of poly (HFP/TFE) for a productivity of 2.0 kg/L/hr. One gram of polymer was soluble in 5 ml of room temperature FC-75 with a trace of insoluble haze. Fluorine NMR in the melt at 320° C. found 44 wt % HFP/56 wt % TFE with 1.3% of the HFP methines as triads. GPC in FC-75 at 80° C. found Mw=629,000, Mn=251,000, Mv=566,000. Inherent viscosity in FC-75 at 25° C. was 0.365. Roughly 69 g of polymer were made/g of $CF_3CF_2CF_2C(CF_3)_2NF_2$ initiator.

EXAMPLE 67

$(CF_3)_2CFN=NCF(CF_3)_2$ Initiation

The 10 cc shaken autoclave was set up as in Example 1. Instead of using $NF_3$ as initiator, a solution of 0.3 ml $(CF_3)_2CFN=NCF(CF_3)_2$ dissolved in 2.0 ml of HFP cyclic dimer (perfluorodimethylcyclobutane) was introduced to 1 gallon reservoir 2 prior to the start of the run. A mix of this initiator with 115 g of TFE and 2000 g of HFP was run through the 10 ml agitated reactor at 11 g/min at 350° C. (estimated residence time 1.0 min) and 96.5 MPa for 145 minutes. After vacuum pump drying at room temperature, this gave 77.6 g of poly (HFP/TFE) for a productivity of 3.2 kg/L/hr. One gram of polymer gave a hazy, quite viscous solution in 5 ml FC-75 at room temperature. Fluorine NMR in the melt at 340° C. found 53 wt % HFP/47 wt % TFE with 8.3% of the HFP methines as triads. GPC in FC-75 at 80° C. found Mw=599,000, Mn=229,000, Mv=541,000. Inherent viscosity in FC-75 at 25° C. was 0.540. Roughly 195 g of polymer were made per gram of $(CF_3)_2CFN=NCF(CF_3)_2$ initiator.

EXAMPLE 68

$(CF_3)_2CFN=NCF(CF_3)_2$ Initiation

The 10 cc shaken autoclave was set up as in Example 1. Instead of using $NF_3$ as initiator, a solution of 0.6 g $(CF_3)_2CFN=NCF(CF_3)_2$ dissolved in 2.0 ml of HFP cyclic dimer (perfluorodimethylcyclobutane) was introduced to 1 gallon reservoir 2 prior to the start of the run. A mix of this initiator with 114 g of TFE and 2000 g of HFP was run through the 10 ml agitated reactor at 12 g/min at 275° C. (estimated residence time 1.1 min) and 96.5 MPa for 160 minutes. After vacuum pump drying at room temperature, this gave 59.7 g of poly (HFP/TFE) for a productivity of 2.2 kg/L/hr. The polymer was soluble in FC-75. Fluorine NMR in the melt at 275° C. found 46 wt % HFP/54 wt % TFE with 2.1% of the HFP methines as triads. GPC in FC-75 at 80° C. found Mw=477,000, Mn=124,000, Mv=413,000. Inherent viscosity in FC-75 at 25° C. was 0.614. Roughly 110 g of polymer were made per gram of $(CF_3)_2CFN=NCF(CF_3)_2$ initiator.

EXAMPLE 69

$(CF_3)_2CFN=NCBr(CF_3)_2$ Initiation

The 10 cc shaken autoclave was set up as in Example 1. Instead of using $NF_3$ as initiator, a solution of 0.5 ml $(CF_3)_2CFN=NCBr(CF_3)_2$ dissolved in 2.0 ml of HFP cyclic dimer (perfluorodimethylcyclobutane) was introduced to 1 gallon reservoir 2 prior to the start of the run. A mix of this initiator with 116 g of TFE and 2000 g of HFP was run through the 10 ml agitated reactor at 11 g/min at 275° C. (estimated residence time 1.2 min) and 96.5 MPa for 110 minutes. After vacuum pump drying at room temperature, this gave 50.5 g of poly (HFP/TFE) for a productivity of 2.7 kg/L/hr. One gram of polymer in 5 ml of room temperature FC-75 gave a highly viscous, hazy solution in FC-75 with perhaps significant amounts of polymer still present as swollen gel. Fluorine NMR in the melt at 340° C. found 48 wt % HFP/52 wt % TFE with 5.0% of the HFP methines as triads. GPC in FC-75 at 80° C. found Mw=569,000, Mn=185,000, Mv=508,000. Inherent viscosity in FC-75 at 25° C. was 0.557. Roughly 95 g of polymer were made per gram of $(CF_3)_2CFN=NCBr(CF_3)_2$ initiator.

EXAMPLE 70

N-Fluoroperfluoropiperidine Initiation

The 10 cc shaken autoclave was set up as in Example 1. Instead of using $NF_3$ as initiator, a solution of 0.3 ml N-fluoroperfluoropiperidine dissolved in 2.0 ml of HFP cyclic dimer (perfluorodimethylcyclobutane) was introduced to 1 gallon reservoir 2 prior to the start of the run. A mix of this initiator with 115 g of TFE and 2000 g of HFP was run through the 10 ml agitated reactor at 14 g/min at 350° C. (estimated residence time 0.8 min) and 96.5 MPa for 110 minutes. After vacuum pump drying at room temperature, this gave 100.2 g of poly (HFP/TFE) for a productivity of 5.4 kg/L/hr. The polymer was soluble in FC-75. Fluorine NMR in the melt at 340° C. found 50 wt % HFP/50 wt % TFE with 2.6% of the HFP methines as triads. GPC in FC-75 at 80° C. found Mw=445,000, Mn=181,000, Mv=398,000. Inherent viscosity in FC-75 at 25° C. was 0.461. Roughly 230 g of polymer were made per gram of N-fluoroperfluoropiperidine initiator.

EXAMPLE 71

$CF_3C(C_2F_5)_2CF(CF_3)_2$ Initiation

The 10 cc shaken autoclave was set up as in Example 1. Instead of using $NF_3$ as initiator, a solution of 1.0 ml $CF_3C(C_2F_5)_2CF(CF_3)_2$ dissolved in 2.0 ml of HFP cyclic dimer (perfluorodimethylcyclobutane) was introduced to 1 gallon reservoir 2 prior to the start of the run. A mix of this initiator with 113 g of TFE and 2000 g of HFP was run through the 10 ml agitated reactor at 10 g/min at 350° C. (estimated residence time 1.1 min) and 96.5 MPa for 106 minutes. After vacuum pump drying at room temperature, this gave 105.6 g of poly (HFP/TFE) for a productivity of 6.0 kg/L/hr. One gram of polymer gave a clear, attractive solution in 5 ml of FC-75 at room temperature. Fluorine NMR in the melt at 340° C. found 58 wt % HFP/42 wt % TFE with ~7% of the HFP methines as triads. GPC in FC-75 at 80° C. found Mw=199,000, Mn=93,000, Mv=179,000. Inherent viscosity in FC-75 at 25° C. was 0.247. Approximately 100 g of polymer were made per gram of $CF_3C(C_2F_5)_2CF(CF_3)_2$ initiator.

Running an identical polymerization but at 275° C. gave 73.4 g of polymer after 145 minutes with an average monomer flow rate of 11 g/min. This polymer analysed for 50 wt % HFP/50 wt % TFE and 5.5% triads by fluorine NMR at 320° C.; Mw=239,000, Mn=82,900, and Mv=206,000 by GPC; inherent viscosity=0.391 at 25° C.; and a productivity of 3.0 kg/L/hr. Roughly 51 g of polymer were made per gram of initiator.

*$CF_3C(C_2F_5)_2CF(CF_3)_2$: 88% $CF_3C(C_2F_5)_2CF(CF_3)_2$ and 12% $[(CF_3)_2CF]_2CFCF_2CF_3$ which is assumed to be an inactive component

EXAMPLE 72

$[(CF_3)_2CF]_2C\!=\!CFCF_3$ Initiation

The 10 cc shaken autoclave was set up as in Example 1. Instead of using $NF_3$ as initiator, a solution of 2.0 ml $[(CF_3)_2CF]_2C\!=\!CFCF_3$*, dissolved in 2.0 ml of HFP cyclic dimer (perfluorodimethylcyclobutane), was introduced to 1 gallon reservoir 2 prior to the start of the run. A mix of this initiator with 116 g of TFE and 2000 g of HFP was run through the 10 ml agitated reactor at 10 g/min at 350° C. (estimated residence time 1.2 min) and 96.5 MPa for 112 minutes. After vacuum pump drying at room temperature, this gave 34.4 g of poly (HFP/TFE) for a productivity of 1.8 kg/L/hr. The polymer gave a highly viscous, hazy solution in FC-75. Fluorine NMR in the melt at 225° C. found 52 wt % HFP/48 wt % TFE with 2.5% of the HFP methines as triads. Inherent viscosity in FC-75 at 25° C. was 0.806. Roughly 16 g of polymer were made per gram of initiator.

*$[(CF_3)_2CF]_2C\!=\!CFCF_3$: 25% $[(CF_3)_2CF]_2C\!=\!CFCF_3$, 72.5% $[(CF_3)_2CF](C_2F_5)C\!=\!C(CF_3)_2$, 1.5% $[(CF_3)_2CF]CF\!=\!C(CF_3)(CF_2CF_2CF_3)$

EXAMPLE 73

$C_2F_5SO_2C_2F_5$ Initiation

A. Initiation at 275° C.: The 10 cc shaken autoclave was set up as in Example 1. Instead of using $NF_3$ as initiator, a solution of 0.5 ml $C_2F_5SO_2C_2F_5$ (~0.95 g) dissolved in 2.0 ml of HFP cyclic dimer (perfluorodimethylcyclobutane) was introduced to 1 gallon reservoir 2 prior to the start of the run. A mix of this initiator with 111 g of TFE and 2000 g of HFP was run through the 10 ml agitated reactor at 12 g/min at 275° C. (estimated residence time 0.96 min) and 96.5 MPa for 150 minutes. After vacuum pump drying at room temperature, this gave 47 g of poly(HFP/TFE) for a productivity of 1.9 kg/L/hr. At 1 g of polymer per 5 ml of FC-75, an extremely viscous solution or near gel was obtained at room temperature. Fluorine NMR in the melt at 340° C. C. found 45 wt % HFP/55 wt % TFE with with 4.2% of the HFP methines as triads. GPC in FC-75 at 80° C. found Mw=892,000, Mn=187,000, Mv=776,000. Inherent viscosity in FC-75 at 25° C. was 0.931. Roughly 58 g of polymer were made per gram of $C_2F_5SO_2C_2F_5$ initiator.

B. Initiation at 350° C.): The 10 cc shaken autoclave was set up as in Example 1. Instead of using $NF_3$ as initiator, a solution of 0.5 ml $C_2F_5SO_2C_2F_5$ (~0.95 g) dissolved in 2.0 ml of HFP cyclic dimer (perfluorodimethylcyclobutane) was introduced to 1 gallon reservoir 2 prior to the start of the run. A mix of this initiator with 112 g of TFE and 2000 g of HFP was run through the 10 ml agitated reactor at 12 g/min at 350° C. (estimated residence time 0.96 min) and 96.5 MPa for 135 minutes. After vacuum pump drying at room temperature, this gave 97.6 g of poly (HFP/TFE) for a productivity of 4.3 kg/L/hr. One gram of polymer gave an attractive, clear solution in 5 ml of FC-75 at room temperature. Fluorine NMR in the melt at 340° C. found 55 wt % HFP/45 wt % TFE. GPC in FC-75 at 80° C. found Mw=374,000, Mn=152,000, Mv=326,000. Inherent viscosity in FC-75 at 25° C. was 0.408. Roughly 130 g of polymer were made per gram of $C_2F_5SO_2C_2F_5$ initiator.

C. Initiation at 400° C.: The 10 cc shaken autoclave was set up as in Example 1. Instead of using $NF_3$ as initiator, a solution of 1.03 g $C_2F_5SO_2C_2F_5$ dissolved in 2.0 ml of HFP cyclic dimer (perfluorodimethylcyclobutane) was introduced to 1 gallon reservoir 2 prior to the start of the run. A mix of this initiator with 151 g of TFE and 2000 g of HFP was run through the 10 ml agitated reactor at ~13–26 g/min at 400° C. (estimated residence time ~0.5 to 1 min) and 96.5 MPa for 85 minutes. Vacuum pump drying first at room temperature and then for four hours at 150° C. gave 190 g of poly (HFP/TFE) for a productivity of 15 kg/L/hr. Dissolving 1 g in 5 ml of FC-75 at room temperature gave a clear viscous solution, the most attractive solution of any of the 400° C. samples. Fluorine NMR in the melt at 320° C. found 58 wt % HFP/42 wt % TFE. GPC in FC-75 at 80° C. found Mw=307,000, Mn=111,000, Mv=274,000. Approximately 90 to 180 g of polymer were made per gram of $C_2F_5SO_2C_2F_5$ initiator.

EXAMPLE 74 n-Perfluorohexyl Iodide Initiation

The 10 cc shaken autoclave was set up as in Example 1. Instead of using $NF_3$ as initiator, a solution of 0.5 ml n-perfluorohexyl iodide dissolved in 2.0 ml of HFP cyclic dimer (perfluorodimethylcyclobutane) was introduced to 1 gallon reservoir 2 prior to the start of the run. A mix of this initiator with 113 g of TFE and 2000 g of HFP was run through the 10 ml agitated reactor at 9 g/min at 350° C. (estimated residence time 1.3 min) and 96.5 MPa for 90 minutes. After vacuum pump drying at room temperature, this gave 39.6 g of poly (HFP/TFE) for a productivity of 2.6 kg/L/hr. One gram of polymer gave a hazy solution with a trace of particulates in 5 ml of FC-75 at room temperature. Fluorine NMR in the melt at 340° C. found 56 wt % HFP/44 wt % TFE with 5% of the HFP methines as triads. GPC in FC-75 at 80° C. found Mw=472,000, Mn=119,000, Mv=401,000. Inherent viscosity in FC-75 at 25° C. was 0.254. A NMR sample heated to 340° C. turned dark purple indicating the incorporation of iodine into the polymer although no iodine color was detected in a melt index sample heated only to 200° C. (melt index$_{200°\ C.,\ 5\ kg}$=4 g/min). Roughly 100 g of polymer were made per gram of initiator.

EXAMPLE 75

2-Iodoheptafluoropropane Initiation

The 10 cc shaken autoclave was set up as in Example 1. Instead of using $NF_3$ as initiator, a solution of 0.7 g 2-iodoheptafluoropropane dissolved in 2.0 ml of HFP cyclic dimer (perfluorodimethylcyclobutane) was introduced to 1 gallon reservoir 2 prior to the start of the run. A mix of this initiator with 114 g of TFE and 2000 g of HFP was run through the 10 ml agitated reactor at ~13 to 26 g/min at 350° C. (estimated residence time ~0.5 to 1.0 min) and 96.5 MPa for 90 minutes. After vacuum pump drying at room temperature, this gave 102.8 g of poly (HFP/TFE) for a productivity of 6.8 kg/L/hr. The polymer was largely soluble in FC-75, 1 g in 5 ml FC-75 giving a hazy solution with residual flocculent solid at room temperature. Fluorine NMR in the melt at 340° C. found 56 wt % HFP/44 wt % TFE. GPC in FC-75 at 80° C. found Mw=157,000, Mn=48,400, Mv=135,000. Roughly 130 to 270 g of polymer were formed per gram of 2-iodoheptafluoropropane initiator.

EXAMPLE 76

1,6-Diiodododecafluorohexane Initiation

A. 1XI(CF$_2$)$_6$I: The 10 cc shaken autoclave was set up as in Example 1. Instead of using NF$_3$ as initiator, a solution of 1.28 g 1,6-diiodododecafluorohexane dissolved in 2.0 ml of HFP cyclic dimer (perfluorodimethylcyclobutane) was introduced to 1 gallon reservoir 2 prior to the start of the run. A mix of this initiator with 224 g of TFE and 4000 g of HFP was run through the 10 ml agitated reactor at 12.5 g/min at 350° C. (estimated residence time 1.0 min) and 96.5 MPa for 238 minutes. After vacuum pump drying at room temperature, this gave 180 g of poly (HFP/TFE) for a productivity of 4.5 kg/L/hr. One gram of polymer gave a solution with trace flocculent solids in 5 ml FC-75 at room temperature. Fluorine NMR in the melt at 320° C. found 59 wt % HFP/41 wt % TFE, the polymer sample turning pink with heating to 320° C. GPC in FC-75 at 80° C. found Mw=221,000, Mn=76,500, Mv=190,000. Roughly 200 g of polymer were formed per gram of 1,6-diiodododecafluorohexane initiator.

B. 10XI(CF$_2$)$_6$I: The 10 cc shaken autoclave was set up as in Example 1. Instead of using NF$_3$ as initiator, 12.8 g 1,6-diiodododecafluorohexane was introduced to 1 gallon reservoir 2 prior to the start of the run. A mix of this initiator with 222 g of TFE and 4000 g of HFP was run through the 10 ml agitated reactor at 36.5 g/min at 350° C. (estimated residence time 0.3 min) and 96.5 MPa for 105 minutes. Vacuum drying at room temperature gave 134 g of poly (HFP/TFE) for a productivity of 7.6 kg/L/hr. The polymer was soluble in FC-75, 1 g in 5 ml FC-75 giving a hazy solution with residual flocculent solid at room temperature. Fluorine NMR in the melt at 320° C. found 47 wt % HFP/53 wt % TFE, the polymer sample turning deep purple with heating to 320° C. GPC in FC-75 at 80° C. found Mw=94,800, Mn=20,300, Mv=66,700. Roughly 11 g of polymer were formed per gram of 1,6-diiodododecafluorohexane initiator.

EXAMPLE 77

(C$_4$F$_9$)$_2$NF Initiation

The 10 cc shaken autoclave was set up as in Example 1. Instead of using NF$_3$ as initiator, a solution of 0.5 ml (C$_4$F$_9$)$_2$NF dissolved in 2.0 ml of HFP cyclic dimer (perfluorodimethylcyclobutane) was introduced to 1 gallon reservoir 2 prior to the start of the run. A mix of this initiator with 114 g of TFE and 2000 g of HFP was run through the 10 ml agitated reactor at 11 g/min at 350° C. (estimated residence time 1.0 min) and 96.5 MPa for 115 minutes. After vacuum pump drying at room temperature, this gave 80.2 g of poly (HFP/TFE) for a productivity of 4.2 kg/L/hr. One gram of polymer gave a hazy solution in 5 ml of FC-75 at room temperature. Fluorine NMR in the melt at 320° C. found 57 wt % HFP/43 wt % TFE with 8.0% of the HFP methines as triads. GPC in FC-75 found Mw=426,000, Mn=187,000, Mv=378,000. Inherent viscosity in FC-75 at 25° C. was 0.380. Roughly 150 g of polymer were made per gram of (C$_4$F$_9$)$_2$NF initiator.

When the polymer sample prepared here was heated at 10° C./min under N$_2$, about 7% weight loss occurred between 50° and 130° C. Weight then stayed steady up until 320° C., at which point another ~10% weight loss occurred between ~320° and 420° C. and finally ~70% by 500° C., the processes between 320° and 500° C. presumably reflecting breaking of the polymer backbone. This onset of backbone degradation at 320° C. is one of the reasons we are surprised that attractive high MW polymer can be made up to at least 400° C. The volatiles lost between 50° and 130° C. were identified as largely perfluoromethylcyclobutane by infrared comparison to a genuine sample. If one wishes, virtually all of the perfluoromethylcyclobutane can be removed from a ~1:1 HFP copolymer sample by heating for several hours at ~150° C. in a vacuum oven. The amount of perfluoromethylcyclobutane retained by polymer samples will reflect polymerization conditions (to what extent polymerization conditions favor the cycloaddition of TFE to HFP as a side reaction) as well as the conditions under which the polymer sample is collected (pressure, temperature, etc.). Once in the polymer sample, pefluoromethylcyclobutane is retained quite tightly. For many purposes, however, perfluoromethylcyclobutane can be considered an innocuous inert.

EXAMPLE 78

NF$_3$ Initiation (Example of Initiation at 350° C.)

A. About 12:1 HFP: TFE, 1X NF$_3$: The 10 cc shaken autoclave was set up as in Example 1. The 25 ml loop (1) off the feed line to reservoir (2) was pressured to 345 kPa (gauge) with nitrogen trifluoride at ambient temperature. A mix of this initiator with 218 g of TFE and 4000 g of HFP was run through the 10 ml agitated reactor at 13 g/min at 350° C. (estimated residence time 0.9 min) and 96.5 MPa for 288 minutes. After vacuum pump drying at room temperature, this gave ~302 g of poly (HFP/TFE) for a productivity of ~6 kg/L/hr. One gram of polymer gave a solution with trace haze in 5 ml of FC-75 at room temperature. Fluorine NMR in the melt at 320° C. found 58 wt % HFP/42 wt % TFE with 8% of the HFP methines as triads. GPC in FC-75 at 80° C. found Mw=235,000, Mn=74,200, Mv=198,000. Inherent viscosity in FC-75 at 25° C. was 0.274. Roughly 1030 g of polymer were made per gram of NF$_3$ initiator.

B. About 12:1 HFP: TFE, 9X NF$_3$: The polymerization above was repeated increasing the concentration of NF$_3$ initiator ~9 times while keeping other variables roughly the same. The 10 cc shaken autoclave was set up as in Example 1. The 25 ml loop (1) off the feed line to reservoir (2) was pressured to 3.13 MPa (gauge) with nitrogen trifluoride at ambient temperature. A mix of this initiator with 228 g of TFE and 4000 g of HFP was run through the 10 ml agitated reactor at 11 to 22 g/min at 350° C. (estimated residence time ~0.5 to 1.1 min) and 96.5 MPa for 315 minutes. After vacuum pump drying at room temperature, this gave 384 g of poly(HFP/TFE) for a productivity of ~7.3 kg/L/hr. One gram of polymer gave a clear solution in 5 ml of FC-75 at room temperature. Fluorine NMR in the melt at 340° C. found 56 wt % HFP/44 wt % TFE with 10% of the HFP methines as triads. GPC in FC-75 at 80° C. found Mw=212, 000, Mn=81,000, Mv=182,000. Inherent viscosity in FC-75 at 25° C. was 0.181. Approximately 100 to 200 g of polymer were made per gram of $NF_3$ initiator.

C. About 16:1 HFP: TFE, 2X $NF_3$: The 10 cc shaken autoclave was set up as in Example 1. The 25 ml loop (1) off the feed line to reservoir (2) was pressured to 758 kPa (gauge) with nitrogen trifluoride at ambient temperature. A mix of this initiator with 169 g of TFE and 4000 g of HFP was run through the 10 ml agitated reactor at 13 g/min at 350° C. (estimated residence time 0.9 min) and 96.5 MPa for 252 minutes. After vacuum pump drying at room temperature, this gave ~215 g of poly (HFP/TFE) for a productivity of ~5 kg/L/hr. One gram of polymer gave a clear solution in 5 ml FC-75 at room temperature. Fluorine NMR in the melt at 320° C. found 58 wt % HFP/42 wt % TFE with 9% of the HFP methines as triads. Inherent viscosity in FC-75 at 25° C. was 0.216. Roughly 440 grams of polymer were made per gram of initiator.

D. About 24:1 HFP: TFE, 2X $NF_3$: The 10 cc shaken autoclave was set up as in Example 1. The 25 ml loop (1) off the feed line to reservoir (2) was pressured to 758 kPa (gauge) with nitrogen trifluoride at ambient temperature. A mix of this initiator with 112 g of TFE and 4000 g of HFP was run through the 10 ml agitated reactor at 12 g/min at 350° C. (estimated residence time 1.0 min) and 96.5 MPa for 300 minutes. Vacuum pump drying at room temperature and then overnight under vacuum at 150° C. gave 140 g of poly (HFP/TFE) for a productivity of ~3 kg/L/hr. One gram of polymer gave a clear solution in 5 ml of FC-75 at room temperature. Fluorine NMR in the melt at 320° C. found 62 wt % HFP/38 wt % TFE with 7% of the HFP methines as triads. GPC in FC-75 at 80° C. found Mw=128,000, Mn=32, 800, Mv=105,000. Inherent viscosity in FC-75 at 25° C. was 0.187. Roughly 260 g of polymer were made per gram of $NF_3$ initiator.

EXAMPLE 79

$NF_3$ Initiation (Initiation at 400° C.)

The 10 cc shaken autoclave was set up as in Example 1. The 25 ml loop (1) off the feed line to reservoir (2) was pressured to 345 kPa (gauge) with nitrogen trifluoride at ambient temperature. A mix of this initiator with 154 g of TFE and 2000 g of HFP was run through the 10 ml agitated reactor at 10 g/min at 400° C. (estimated residence time 1.2 min) and 96.5 MPa for 55 minutes. Vacuum pump drying at room temperature and then for 4 hours at 150° C. gave 53 g of poly (HFP/TFE) for a productivity of 4.8 kg/L/hr. One gram polymer was soluble in 5 ml of FC-75 at room temperature with residual haze. Fluorine NMR in the melt at 320° C. found 53 wt % HFP/47 wt % TFE with 4% of the HFP methines as triads. GPC in FC-75 at 80° C. found Mw=173,000, Mn=47,300, Mv=138,000. Roughly 620 g of polymer were made per gram of $NF_3$ initiator.

EXAMPLE 80

$C_4F_9SSC_4F_9$ Initiation (Initiation at 350° and 400° C.)

A. At 350° C.: The 10 cc shaken autoclave was set up as in Example 1. Instead of using $NF_3$ as initiator, a solution of 0.5 ml $C_4F_9SSC_4F_9$ dissolved in 2.0 ml of HFP cyclic dimer (perfluorodimethylcyclobutane) was introduced to 1 gallon reservoir 2 prior to the start of the run. A mix of this initiator with 113 g of TFE and 2000 g of HFP was run through the 10 ml agitated reactor at 11 g/min at 350° C. (estimated residence time 1.0 min) and 96.5 MPa for 150 minutes. After vacuum pump drying at room temperature, this gave 50.23 g of poly (HFP/TFE) for a productivity of 2.0 kg/L/hr. Consistent with its high molecular weight, 1 gram of polymer gave an extremely viscous, partial solution in 5 ml of FC-75 at room temperature. Fluorine NMR in the melt at 340° C. found 50 wt % HFP/50 wt % TFE with 14.0% of the HFP methines as triads. GPC in FC-75 at 80° C. found Mw=1,108,000, Mn=238,000, Mv=976,000. Inherent viscosity in FC-75 at 25° C. was 0.946. Roughly 70 g of polymer were made per gram of $C_4F_9SSC_4F_9$ initiator.

B. At 400° C.: The 10 cc shaken autoclave was set up as in Example 1. Instead of using $NF_3$ as initiator, a solution of 0.5 ml $C_4F_9SSC_4F_9$ (0.89 g) dissolved in 2.0 ml of HFP cyclic dimer (perfluorodimethylcyclobutane) was introduced to 1 gallon reservoir 2 prior to the start of the run. A mix of this initiator with 151 g of TFE and 2000 g of HFP was run through the 10 ml agitated reactor at ~12.7 g/min at 400° C. (estimated residence time ~1.0 min) and 96.5 MPa for 85 minutes. After vacuum pump drying at room temperature and then for 4 hours under vacuum at 150° C., 185.9 g of poly (HFP/TFE) were obtained for a productivity of 13.0 kg/L/hr. Mixing 1 g of polymer with 5 ml FC-75 at room temperature gave a viscous solution with residual insolubles. Fluorine NMR in the melt at 320° C. found 54 wt % HFP/46 wt % TFE. GPC in FC-75 at 80° C. found Mw=361,000, Mn=113,000, Mv=306,000. Roughly 210 g of polymer were made per gram of $C_4F_9SSC_4F_9$ initiator.

EXAMPLE 81

$(C_4F_9)_2NSCF_3$ Initiation (Initiation at 350° C.)

The 10 cc shaken autoclave was set up as in Example 1. Instead of using $NF_3$ as initiator, a solution of 0.5 ml $(C_4F_9)_2NSCF_3$ (0.92 g) dissolved in 2.0 ml of HFP cyclic dimer (perfluorodimethylcyclobutane) was introduced to 1 gallon reservoir 2 prior to the start of the run. A mix of this initiator with 80 g of TFE and 2200 g of HFP was run through the 10 ml agitated reactor at ~11 g/min at 350° C. (estimated residence time 1.1 min) and 96.5 MPa for 105 minutes. Vacuum pump drying at room temperature and then for 4 hours at 150° C. gave 97 g of poly (HFP/TFE) for a productivity of 525 kg/L/hr. One gram of polymer gave a viscous solution with residual insolubles when mixed with 5 ml of FC-75 at room temperature. Fluorine NMR in the melt at 320° C. found 55 wt % HFP/45 wt % TFE. GPC in FC-75 at 80° C. found Mw=391,000, Mn=116,000, Mv=332,000. Roughly 210 g of polymer were made per gram of $(C_4F_9)_2NSCF_3$ initiator.

EXAMPLE 82

$(C_4F_9)_3N$ Initiation (Initiation at 350° C. and 400° C.)

A. At 350° C.: The 10 cc shaken autoclave was set up as in Example 1. Instead of using $NF_3$ as initiator, a solution of 0.5 ml $(C_4F_9)_3N$ (0.94 g) dissolved in 2.0 ml of HFP cyclic dimer (perfluorodimethylcyclobutane) was introduced to 1 gallon reservoir 2 prior to the start of the run. A mix of this initiator with 117 g of TFE and 2000 g of HFP was run through the 10 ml agitated reactor at 11 g/min at 350° C. (estimated residence time 1.0 min) and 96.5 MPa for 117 minutes. After vacuum pump drying at room temperature, this gave 25 g of poly (HFP/TFE) for a productivity of 1.3 kg/L/hr. The polymer gave an extremely viscous solution or gel in FC-75. GPC in FC-75 at 80° C. found Mw=1,238,000, Mn=153,000, Mv=1,087,000. Inherent viscosity in FC-75 at 25° C. was 1.375. Roughly 26 g of polymer were made per gram of $(C_4F_9)_3N$ initiator.

B. At 400° C.: The 10 cc shaken autoclave was set up as in Example 1. Instead of using $NF_3$ as initiator, a solution of 0.5 ml $(C_4F_9)_3N$ (0.94 g) dissolved in 2.0 ml of HFP cyclic dimer (perfluorodimethylcyclobutane) was introduced to 1 gallon reservoir 2 prior to the start of the run. A mix of this initiator with 157 g of TFE and 2000 g of HFP was run through the 10 ml agitated reactor at 13 g/min at 400° C. (estimated residence time 0.9 min) and 96.5 MPa for 124 minutes. After vacuum pump drying at room temperature and then for ~15 hours under vacuum at 150° C., 120.0 g of poly (HFP/TFE) were obtained for a productivity of 5.8 kg/L/hr. Mixing 1 g of polymer with 5 ml of FC-75 at room temperature gave a solution with residual insolubles. Fluorine NMR in the melt at 320° C. found 55 wt % HFP/45 wt % TFE. GPC in FC-75 at 80° C. found Mw=289,000, Mn=78,300, Mv=238,000. Roughly 130 g of polymer were made per gram of $(C_4F_9)_3N$ initiator.

EXAMPLE 83

$(C_4F_9)_2NF$ Initiation (Initiation at 275° C.)

The 10 cc shaken autoclave was set up as in Example 1. Instead of using $NF_3$ as initiator, a solution of 0.8 ml $(C_4F_9)_2NF$ (~1.4 g) dissolved in 5 ml of HFP cyclic dimer (perfluorodimethylcyclobutane) was introduced to 1 gallon reservoir 2 prior to the start of the run. A mix of this initiator with 223 g of TFE and 4000 g of HFP was run through the 10 ml agitated reactor at 12 g/min at 275° C. (estimated residence time 1.1 min) and 96.5 MPa for 315 minutes. After vacuum pump drying at room temperature, this gave 146 g of poly (HFP/TFE) for a productivity of 2.8 kg/L/hr. At room temperature 1 g of polymer dissolved in 5 ml of FC-75. Fluorine NMR in the melt at 340° C. found 47 wt % HFP/53 wt % TFE with 7.4% of the HFP methines as triads. GPC in FC-75 at 80° C. found Mw=603,000, Mn=226,000, Mv=546,000. Inherent viscosity in FC-75 at 25° C. was 0.679. Roughly 110 g of polymer were made per gram of $(C_4F_9)_2NF$ initiator.

EXAMPLE 84

NO ADDED INITIATOR (Initiator Free Runs at 350° C. and 400° C.)

A. At 350° C.: The 10 cc shaken autoclave was set up as in Example 1. No initiator at all was added. A mix of 113 g of TFE and 2000 g of HFP was run through the 10 ml agitated reactor at 11 g/min at 350° C. (estimated residence time 1.0 min) and 96.5 MPa for 115 minutes. After vacuum pump drying at room temperature, this gave 17.2 g of poly (HFP/TFE) for a productivity of 0.90 kg/L/hr. Rolling 1 g of polymer with 5 ml of FC-75 at room temperature gave a hazy viscous solution. Fluorine NMR in the melt at 340° C. found 57 wt % HFP/43 wt % TFE. GPC in FC-75 at 80° C. found Mw=451,000, Mn=147,000, Mv=397,000.

B. At 400° C. The 10 cc shaken autoclave was set up as in Example 1. No initiator at all was added. A mix of 154 g of TFE and 2000 g of HFP was run through the 10 ml agitated reactor at 12 g/min at 400° C. (estimated residence time 1.0 min) and 96.5 MPa for 110 minutes. After vacuum pump drying first at room temperature and then for four hours at 150° C., 77.9 g of poly (HFP/TFE) were obtained for a productivity of 4.2 kg/L/hr. Rolling 1 g of polymer with 5 ml of FC-75 at room temperature gave a hazy solution. Fluorine NMR in the melt at 320° C. found 57 wt % HFP/43 wt % TFE. GPC in FC-75 at 80° C. found Mw=262,000, Mn=69,900, Mv=208,000.

EXAMPLE 85

TFE/HFP Copolymerization in a Well Stirred Reactor

Three separate feed streams were converted to gases and metered into a mixing vessel typically at 350–380 kPa. The mixture was then compressed in two stages to goal pressures. The compressed super-critical fluid was fed to a preheater, held at 175° to 200° C. in these experiments, and then into a stainless steel well-mixed reactor of 100 ml volume provided with a mechanical stirrer running at 1100 rpm. The design of this feed system assures that the flows are uniform and well controlled, since they are all handled as gases and compressed together.

From the reactor the polymer solution flows through a reducing valve, which was also used to control reactor pressure at 96.5 MPa, and thence into an enclosed collection vessel at 156 kPa where the unreacted monomers are allowed to evaporate. The evaporated monomers are condensed and collected in a separate system. Product was removed from the collection vessel at the end of the run.

Typical example conditions are shown in the following table which also shows the properties of the resulting product.

|  | Units | Run A | Run B |
|---|---|---|---|
| Feed 1: (100% HFP) | Kg/hr | 4.7 | 5.03 |
| Feed 2: |  |  |  |
| Wt. % $NF_3$ in HFP | Wt. % | 1.32 | 2.49 |
| Rate | Kg/hr | 0.045 | 0.049 |
| Feed 3: (100% TFE) | Kg/hr | 0.21 | 0.20 |
| Mixer Pressure | kPa | 356 | 377 |
| Preheater Temperature | °C. | 175 | 200 |
| Reactor Temperature | °C. | 267 | 275 |
| Polymerization Reactor Pressure | MPa | 96.5 | 96.5 |
| Production rate | gm/hr | 168 | 196 |
| Product properties: |  |  |  |
| Wt percent HFP | % | 54.7 | 58.9 |
| Molecular weight Mn |  | 113,000 | 71,600 |
| Molecular weight Mw |  | 325,000 | 170,000 |
| Mw/Mn |  | 2.87 | 2.37 |
| Calculated TFE conversion | % | 36.2 | 40.3 |

EXAMPLE 86

$CF_3CF_2CF_2C(CF_3)_2NF_2$

A: A 2 liter r.b. flask with a stirring bar was charged with 75 g of dry, ball-milled KF in a glove box. The flask was transferred to a hood, swept with nitrogen, and 1 liter of 4A molecular sieve dried dimethylformamide added with with stirring. The contents of the flask were chilled to −12° C. and the addition of phenyldiazonium tetrafluoroborate was begun. Soon into the addition the contents of the flask were further chilled to −37° C. and phenyldiazordum tetrafluoroborate addition continued, a total of 282.9 g being added.

With the temperature at −35° to −40° C., 325.3 g of $(CF_3)_2C=CFCF_2CF_3$ were added in a trickle, then 27.2 g of dry KF, and finally another 119.6 g of $(CF_3)_2C=CFF_2CF_3$. As the last of the $(CF_3)_2C=CFF_2CF_3$ was run in, temperature increased to −31° C. and foaming increased. The reaction mixture was chilled to and held at −38° C. for an hour. Temperature was allowed then to gradually rise to room temperature. The reaction mixture was stirred overnight at room temperature under nitrogen. The solids were filtered off and washed with ether. The filtrate was taken up in about 2 liters of ether, washed with water, 5× with 5% NaOH, 4× with 5% HCl, each aqueous wash back-washed with 1 liter of ether. The ether layer was washed with saturated sodium chloride, dried over $CaCl_2$, and concentrated on a rotary evaporator. This gave 283.6 g of crude dark red oil. This oil was dissolved in 500 g of trifluoroacetic acid. Reduction was quite slow taking the addition of 54 g amalgamated zinc, 44 g of amagamated zinc four days later, 300 g trifluoroacetic acid and 40 g amalgamated zinc about 23 days later, and then an additional 15 day wait. The reaction mixture was worked up by adding 1 liter of distilled water and steam distilling directly out of the flask. Steam distillation accompanied by foaming gave 152.7 g of crude $CF_3CF_2CF_2C(CF_3)_2NH_2$ using a Dean-Stark trap for collection. Three such batches (totaling ~360 g) ranging in GC purity from 79 to 96% were combined and added slowly to 50 ml $Et_2NH$ mixed with 100 ml 40% aqueous KOH (exotherm, slow addition). After stirring overnight, the reaction mixture was poured into water, washed several times with 5% HCl, and dried. Attempted distillation at this point gave fumes and discoloration and was discontinued. The reaction mixture was added to a solution made by dissolving 133 g of 85% KOH in 150 ml water and 500 ml ethanol. This mixture was stirred overnight and then refluxed over the next night. Water was added to nearly fill the 2 liter reaction flask and then the contents steam distilled. This distillate was washed with water and the lower layer, 284.8 g, then dried over $CaCl_2$. The fluorine NMR was very clean while GC showed a short retention time impurity with an area of 8.7%. This $CF_3CF_2CF_2C(CF_3)_2NH_2$ was used in step B below.

B.: A 60 ml Teflon® bottle was loaded with 9.62 g of $CF_3CF_2CF_2C(CF_3)_2NH_2$. Over a period of 4.55 hr, 1726 ml of $F_2$ gas was passed into the bottle at atmospheric pressure and room temperature while stirring the contents gently. The reaction mixture was let stand overnight at room temperature. A pipet was used to withdraw 8.33 g of light yellow fluid from the Teflon® bottle. Fluorine NMR was consistent with quantitative conversion to the desired $CF_3CF_2CF_2C(CF_3)_2NF_2$: +36.0 ppm (1.9 F), −62.3 ppm (6.0 F), −81.0 ppm (3.05 F), −109.2 ppm (1.9 F), −123.3 ppm (2.0 F). No other adsorptions were visible in the fluorine NMR, yield 78%. In a similar, larger scale run, a center cut of colorless distillate was taken off a little NaF ($bp_{760}$=84°–88° C.).

Calc. for $C_6F_{13}NF_2$: 19.42C 76.80F 3.78N Found: 19.35C 76.93F 3.71N

EXAMPLE 87

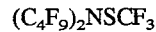

A 100 ml flask was charged with $C_4F_9N=CFC_3F_7$ (5.0 g 11.5 mmol), CsF (2.3 g, 15 mmol), and 10 ml of diethyl ether under a $N_2$ atmosphere. After stirring for 3 hours at room temperature, the mixture was cooled to ~5° C. by an ice-water bath and $CF_3SCl$ (excess) added via a dry ice-acetone condenser until a slight yellow color was observed in the mixture. The resulting mixture was stirred at room temperature for one day. Then the mixture was filtered, the filtrate partially distilled to remove ether, and the residue bulb-to-bulb distilled at reduced pressure to afford 4.8 g (75%) of colorless liquid, a small amount of which when heated in a melting point capillary showed the initiation of boiling at ~145° C. $^{19}F$ NMR was consistent with the desired product $(C_4F_9)_2NSCF_3$: −50.1 (m, 3F), −81.4 (t, J=10 Hz, 6F), −86.0 (AB q, J=233 Hz, 4F), −121.0 (AB q, J=290 Hz, 4F), −126.9 (t, J=15 Hz, 4F).

Monomers for High Temperature Polymerization

Experimental

New monomer combinations are described in Examples 88–111 below. Polymerizations were run in a semicontinuous fashion using the equipment and general methods described in Example 1. Weights of TFE added to the mixing reservoir were calculated the same way as in Examples 66 and 84. In cases where an NMR analysis of polymer composition was not available, elemental analysis was often performed assuming a 1:1 HFP: TFE molar ratio for purposes of calculation. At high levels of incorporation and high temperatures, those termonomers with chain transferring groups often gave greases and oils rather than solid polymer. This includes methyl vinyl ether, propylene, isobutylene, and $CH_3CH_2CH_2CH_2OCF=CF_2$.

Compositions for many of the TFE/HFP copolymers were determined from $^{19}F$ spectra taken either on polymer melts at 300° to 340° C. or on solutions in hexafluorobenzene at 80° C. Integration of the CF peaks at −174 ppm to −185 ppm was used to determine HFP content, and the $CF_2$ absorptions at −100 ppm to −125 ppm, corrected for comonomer contributions, for the TFE content. The termonomer content was determined from the integrated intensities of the relevant signals: $CF_3CF_2CF_2CF_2CH=CH_2$ (Example 97) from the signal at −82.5 ppm, $CF_2=CFOCF_2(CF_3)CF)$ $CF_2CF_2SO_2F$ and $CF_2=CFCF_2OCF_2CF_2SO_2F$ (Examples 94A and 93) from the signal at +46.2 ppm, $CH_2=CHOCOCF_3$ (Example 96) from the signal at −77.5 ppm, $CF_2=CFOCF_2(CF_3)CF)CF_2CF_2SO_2F$ in the melt (Example 94B) using various —OCF absorptions around −75 to −83 and −136 to −140 ppm, $CF_2=CFCF_2CN$ (Example 92) from the signal at −107 ppm, CTFE (Example 91A) from the signals at −129 ppm −134 ppm, $CF_3CH=CH_2$ from the $\overline{CF_3CH}$ signal at −67 ppm, perfluorocyclobutene by difference between the observed exess CF's around −175 to −185 ppm compared to what expected from HFP alone (Example 106), perfluorocyclopentene (Example 107) same as the perfluorocyclobutene, $CF_2=C(CF_3)COF$ from the —COF resonance at about 20 ppm (Example 109), trifluoroethylene from the —CFH— resonance at −199 ppm (Example 110), perfluoro-2-methylene-4-methyl-1,3-dioxolane from the resonances for the —$OCF_2$ and the —$CF_3$ at −80 to −82 ppm (Example 111).

Composition of polymers containing VF2 as the third monomer (Example 88 to 90) were determined from both the $^{19}F$ spectrum and a $^1H$ spectrum taken on a sample of the polymer into which an internal standard, containing both fluorine and protons, had been added. The VF2 $^1H$ signal at 2.2 ppm was ratioed to the internal standard signals, converted into an absolute mount of VF2 which was subtracted from a weighed amount of the polymer to give the amount of polymer which was not VF2. Polymers containing both TFE and HFP along with VF2 determined the TFE and HFP in the way mentioned above.

The composition of polymers containing ethylene as a third monomer (Example 98) were determined from both the $^{19}$F and $^{13}$C spectra taken on solutions in hexafluorobenzene. The $^{19}$F spectrum was used to determine the ratio of the HFP to TFE. The $^{13}$C spectrum was used to determine the integrated intensities of the $CF_2$ signals at 106 ppm–126 ppm, the CF signals at 91 ppm–99 ppm, and the $CH_2$ signals at 20 ppm–28 ppm.

The composition of the HFP/TFE/$CF_3CF=CH_2$ terpolymer was determined by $^{13}$C NMF using the $CH_2$ carbon from 30 and 32 ppm for $CF_3CF=CH_2$, the CF carbon at 98 to 100 ppm for $CF_3CF=CF_2$ after subtraction of the CF contributed by tetrafluoropropene, and the $CF_2$ carbon from 110 to 132 ppm for TFE after subtraction of $CF_3$ and $CF_2$ carbons contributed by hexafluoropropene and tetrafluoropropene (Example 101).

EXAMPLE 88

Continuous Polymerization in 10 ml Autoclave with Agitation HFP/TFE/VF2

The same set up was used as in Example 1. A mixture of 4000 g of HFP, 220 g TFE, 3 g vinylidene fluoride, and about 1.2 g of $NF_3$ was made in 1 gallon reservoir (2). About 3548 g of this mixture were run through the 10 ml shaken autoclave at 250° C. and 14,000 psi over a 275 minute period. Drying the product under vacuum gave 177 g of white polymer. Analysis results are gathered below.

>1 g/5 ml of FC-75, clear solution at room temperature
Mw=299,000 by GPC in FC-75 at 80° C.
Mn=111,000 by GPC in FC-75 at 80° C.
Inherent Viscosity in FC-75 at 25° C.=0.384
Melt index$_{185°\ C., 5\ kg}$=0.7 g/min
Tg=28° C. (second heat) by DSC @10° C./min under $N_2$
Tm, none detected by DSC @10° C./min, $N_2$, second heat
10% weight loss temperature 420° C. @10° C./min under $N_2$
~2 mole % VF2 by $^{19}$F NMR in melt at 320° C.
~39 mole % HFP by $^{19}$F NMR in melt at 320° C.
~59 mole % TFE by $^{19}$F NMR in melt at 320° C.
Productivity 3.8 kg/L/hr (32 lbs/gal/hr)

EXAMPLE 89

Continuous Polymerization in 10 ml Autoclave with Agitation HFP/TFE/VF2

The same set up was used as in Example 1. A mixture of 4000 g of HFP, 164 g TFE, 40 g vinylidene fluoride, and about 1.2 g of $NF_3$ was made in 1 gallon reservoir (2). About 3302 g of this mixture were run through the 10 ml shaken autoclave at 275° C. and 14,000 psi over a 185 minute period. Drying the product under vacuum gave 180 g of white polymer. Analysis results are gathered below.

Little or partial solubility at 1 g/5 ml FC-75, Freon® 113, or acetone at r.t.
Mw=122,000 by GPC in FC-75 at 80° C.
Mn=38,300 by GPC in FC-75 at 80° C.
Inherent Viscosity in FC-75 at 25° C.=0.247 (cloudy solution)
Melt index$_{185°\ C., 5\ kg}$=1 g/min
Tg=2° C. (second heat) by DSC @10° C./min under $N_2$
Tm, none detected by DSC @10° C./min, $N_2$, second heat
10% weight loss temperature 410° C. @10° C./min under $N_2$
~29 mole % VF2 by $^{19}$F NMR in melt at 300° C.
~39 mole % HFP by $^{19}$F NMR in melt at 300° C.
~32 mole % TFE by $^{19}$F NMR in melt at 300° C.
Productivity 5.8 kg/L/hr (49 lbs/gal/hr)

EXAMPLE 90

Continuous Polymerization in 10 ml Autoclave with Agitation HFP/VF2

The same set up was used as in Example 1. A mixture of 2000 g of HFP, 80 g vinylidene fluoride, and about 0.6 g of $NF_3$ was made in 1 gallon reservoir (2). About 1656 g of this mixture were run through the 10 ml shaken autoclave at 250° C. and 14,000 psi over a 139 minute period. Drying the product under vacuum gave 105 g of white polymer. Analysis results are gathered below.

0.1 g/l ml solubility in Freon® 113 or acetone at r.t.
Inherent Viscosity in Freon® 113 at 25° C.=0.044
Tg=–5° C. (second heat) by DSC @10° C./min under $N_2$
Tm, none detected by DSC @10° C./min, $N_2$, second heat
10% weight loss temperature 190° C. @10° C./min under $N_2$
~59 mole % VF2 by $^{19}$F NMR in melt at 300° C.
~41 mole % HFP by $^{19}$F NMR in melt at 300° C.
Productivity 4.5 kg/L/hr (38 lbs/gal/hr)

EXAMPLE 91

Continuous Polymerization in 10 ml Autoclave with Agitation HFP/TFE/CTFE

A. ~124:9.2:1 HFP:TFE:CTFE: The same set up was used as in Example 1. A mixture of 4000 g of HFP, 197 g TFE, 25 g chlorotrifluoroethylene, and about 1.2 g of $NF_3$ was made in 1 gallon reservoir (2). About 4057 g of this mixture were run through the 10 ml shaken autoclave at 250° C. and 14,000 psi over a 266 minute period. Drying the product under vacuum gave 120 g of white polymer. Analysis results are gathered below.

1 g/5 ml soluble in FC-75 at r.t. with a trace of flocculent residue
Mw=171,000 by GPC in FC-75 at 80° C.
Mn=65,300 by GPC in FC-75 at 80° C.
Tg=30° C. (second heat) by DSC @10° C./min under $N_2$
Tm, none detected by DSC @10° C./min, $N_2$, second heat
10% weight loss temperature, 410° C. @10° C./min under $N_2$
2.9 mole % CTFE by $^{19}$F NMR in melt at 320° C.
40.6 mole % HFP by $^{19}$F NMR in melt at 320° C.
56.5 mole % TFE by $^{19}$F NMR in melt at 320° C.
Productivity 2.7 kg/L/hr (22 lbs/gal/hr)

B. ~15:1.2:1 HFP:TFE:CTFE: The same set up was used as in Example 1. A mixture of 2000 g of HFP, 108 g TFE, 100 g chlorotrifluoroethylene, and about 0.6 g of $NF_3$ was made in 1 gallon reservoir (2). About 1913 g of this mixture were run through the 10 ml shaken autoclave at 250° C. and 14,000 psi over a 140 minute period. Drying the product under vacuum gave 107 g of white polymer. Analysis results are gathered below.

1 g/5 ml soluble in FC-75 at r.t., hazy flocculent residue
Mw=39,100 by GPC in FC-75 at 80° C.

Mn=15,300 by GPC in FC-75 at 80° C.

Melt index$_{120° C., 5 kg}$=8 g/min

Tg=26° C. (second heat) by DSC @10° C./min under N$_2$

10% weight loss temperature, 390° C. @10° C./min under N$_2$

Tm, none detected by DSC @10° C./min under N$_2$ 19 mole % CTFE by $^{19}$F NMR in melt at 320° C.

27 mole % HFP by $^{19}$F NMR in melt at 320° C.

54 mole % TFE by $^{19}$F NMR in melt at 320° C.

Productivity 4.6 kg/L/hr (38 lbs/gal/hr)

EXAMPLE 92

Continuous Polymerization in 10 ml Autoclave with Agitation HFP/TFE/NCCF$_2$CF=CF$_2$ The same set up was used as in Example 1. A mixture of 2000 g of HFP, 114 g TFE, 68 g NCCF$_2$CF=CF$_2$, and about 1.2 g of NF$_3$ was made in 1 gallon reservoir (2). About 1912 g of this mixture were run through the 10 ml shaken autoclave at 275° C. and 14,000 psi over a 175 minute period. Drying the product under vacuum gave 32 g of white polymer. Analysis results are gathered below.

1 g soluble 5 ml FC-75 at r.t. with a bit of residual flocculent solids

Mw=58,900 by GPC in FC-75 at 80° C.

Mn=24,800 by GPC in FC-75 at 80° C.

Inherent Viscosity in FC-75 at 25° C.=0.119

Melt index$_{100° C., 5 kg}$=2.4 g/min

Tg=25° C. (second heat) by DSC @10° C./min under N$_2$

Tm, none detected by DSC @10° C./min, N$_2$, second heat

10% weight loss temperature, 410° C. @10° C./min under N$_2$

~0.6 mole % NCCF$_2$CF=CF$_2$ by $^{19}$F NMR, hexafluorobenzene, 80° C.

~37 mole % HFP by $^{19}$F NMR, hexafluorobenzene solution, 80° C.

~62 mole % TFE by $^{19}$F NMR, hexafluorobenzene solution, 80° C.

Productivity 1.1 kg/L/hr (9 lbs/gal/hr)

EXAMPLE 93

Continuous Polymerization in 10 ml Autoclave with Agitation HFP/TFE/FSO$_2$CF$_2$CF$_2$OCF$_2$CF=CF$_2$ The same set up was used as in Example 1. A mixture of 2000 g of HFP, 114 g TFE, 84 g FSO$_2$CF$_2$CF$_2$OCF$_2$CF=CF$_2$, and about 1.2 g of NF$_3$ was made in 1 gallon reservoir (2). About 1125 g of this mixture were run through the 10 ml shaken autoclave at 275° C. and 14,000 psi over a 115 minute period. Drying the product under vacuum gave 61.5 g of white polymer. Of this a 10.9 g sample was dried for another 4 hours at 150° C. in a vacuum oven, giving 10.4 g fused solid with the following analyses. Analysis results are gathered below.

1 g soluble 5 ml FC-75 at r.t. with a bit of residual flocculent solids

Mw=142,000 by GPC in FC-75 at 80° C.

Mn=55,800 by GPC in FC-75 at 80° C.

Inherent Viscosity in FC-75 at 25° C.=0.190

Melt index$_{200° C., 5 kg}$=4 g/min

Tg=26° C. (second heat) by DSC @10° C./min under N$_2$

Tm, none detected by DSC @10° C./min, N$_2$, second heat

10% weight loss temperature 430° C. @10° C./min under N$_2$

~0.25 mole % FSO$_2$CF$_2$CF$_2$OCF$_2$CF=CF$_2$ by $^{19}$F NMR in melt at 150° C.

~37 mole % HFP by $^{19}$F NMR in melt at 150° C.

~63 mole % TFE by $^{19}$F NMR in melt at 150° C.

Productivity 3.0 kg/L/hr (25 lbs/gal/hr)

EXAMPLE 94

Continuous Polymerization in 10 ml Autoclave with Agitation HFP/TFE/FSO$_2$CF$_2$CF$_2$OCF(CF$_3$)CF$_2$OCF=CF$_2$ (PSEPVE)

A. ~240:20:1 HFP:TFE:PSEPVE. The same set up was used as in Example 1. A mixture of 4000 g of HFP, 221 g TFE, 30 mL FSO$_2$CF$_2$CF$_2$OCF(CF$_3$)CF$_2$OCF=CF$_2$, and about 1.2 g of NF$_3$ was made in 1 gallon reservoir (2). About 1639 g of this mixture were run through the 10 ml shaken autoclave at 250° C. and 14,000 psi over a 184 minute period. The polymer was dried under vacuum first at room temperature and then overnight at 150° C. giving 62 g of fused sheet. Analysis results are gathered below.

1 g soluble 5 ml FC-75 at r.t. with a trace of haze

Mw=77,600 by GPC in FC-75 at 80° C.

bin=37,300 by GPC in FC-75 at 80° C.

Inherent Viscosity in FC-75 at 25° C.=0.128

Tg=14° C. (second heat) by DSC @10° C./min under N$_2$

Tm, none detected by DSC @10° C./min, N$_2$, second heat

10% weight loss temperature 380° C. @10° C./min under N$_2$

~0.7 mole % FSO$_2$CF$_2$CF$_2$OCF(CF$_3$)CF$_2$OCF=CF$_2$ by $^{19}$F NMR in hexafluorobenzene solution at 80° C.

~37 mole % HFP by $^{19}$F NMR in hexafluorobenzene solution at 80° C.

~61 mole % TFE by $^{19}$F NMR in hexafluorobenzene solution at 80° C.

1% FSO$_2$CF$_2$CF$_2$OCF(CF$_3$)CF$_2$OCF=CF$_2$ as free monomer by $^{19}$F NMR in hexafluorobenzene solution at 80° C.

Productivity 2.0 kg/L/hr (17 lbs/gal/hr)

B. ~240:30:1 HFP:TFE:PSEPVE. The same set up was used as in Example 1. A mixture of 2667 g of HFP, 224 g TFE, 33 g FSO$_2$CF$_2$CF$_2$OCF(CF$_3$)CF$_2$OCF=CF$_2$, and about 1.2 g of NF$_3$ was made in 1 gallon reservoir (2). About 2527 g of this mixture were run through the 10 ml shaken autoclave at 250° C. and 14,000 psi over a 215 minute period. The polymer was dried under vacuum first at room temperature and then for 4 hours at 150° C. giving 232.9 g. TGA found that about 5 wt % of PSEPVE was still retained by the polymer coming off at about 130°–170° C. The remaining 221.7 g sample of polymer was further dried for 4 hours at 200° C. in a vacuum oven, giving 200.3 g of flexible orange, clear polymer. Analysis results are gathered below.

1 g partially soluble in 5 ml FC-75 at r.t.

Mw=61,600 by GPC in FC-75 at 80° C.

Mn=25,300 by GPC in FC-75 at 80° C.

Tg=15° C. (second heat) by DSC @10° C./min under N$_2$

10% weight loss temperature 390° C. @10° C./min under N$_2$

Tm, none detected by DSC @10° C./min, N$_2$, second heat 0.6 mole % $FSO_2CF_2CF_2OCF(CF_3)CF_2OCF=CF_2$ by $^{19}F$ NMR 320° C.

35.2 mole % HFP by $^{19}F$ NMR in melt at 320° C.

64.2 mole % TFE by $^{19}F$ NMR in melt at 320° C.

Productivity 5.9 kg/L/hr (49 lbs/gal/hr)

EXAMPLE 95

Continuous Polymerization in 10 ml Autoclave with Agitation

HFP/TFE/F-2-Methyl-2,3-dihydro-1,4-dioxin (PMDD)

The same set up was used as in Example 1. A mixture of 1000 g of HFP, 62 g TFE, 24.7 g F-2-Methyl-2,3-dihydro 1,4-dioxin, and about 0.6 g of $NF_3$ was made in 1 gallon reservoir (2). About 650 g of this mixture were run through the 10 ml shaken autoclave at 275° C. and 14,000 psi over a 54 minute period. The polymer was dried under vacuum at room temperature, 53.5 g.

1 g largely soluble 5 ml FC-75 at r.t. with a residue of flocculent solid

Mw=53,600 by GPC in FC-75 at 80° C.

Mn=25,100 by GPC in FC-75 at 80° C.

Inherent Viscosity in FC-75 at 25° C.=0.092

Tg=30° C. (second heat) by DSC @10° C./min under $N_2$

Tm, none detected by DSC @10° C./min, $N_2$, second heat

~0.5 mole % perfluoro(5-methyl-2,3-dihydro-1,4-dioxin) by $^{19}F$ NMR in melt at 300° C.

~45 mole % HFP by $^{19}F$ NMR in melt at 300° C.

~55 mole % TFE by $^{19}F$ NMR in melt at 300° C.

Productivity 5.9 kg/L/hr (49 lbs/gal/hr)

EXAMPLE 96

Continuous Polymerization in 10 ml Autoclave with Agitation HFP/TFE/$CH_2=CHO(C=O)CF_3$ The same set up was used as in Example 1. A mixture of 2000 g of HFP, 113 g TFE, 10 ml (12 g) vinyl trifluoroacetate, and ~1.2 g of $NF_3$ was made in 1 gallon reservoir (2). About 1739 g of this mixture were run through the 10 ml shaken autoclave at 250° C. and 14,000 psi over a 152 minute period. Drying the product under vacuum gave 105.3 g of white polymer, a 10.32 g sample of which was dried further for 4 hours at 150° C. under vacuum, giving 9.9 g of colorless polymer. Results for the oven dried 9.9 g sample are gathered below.

1 g/5 ml FC-75 at r.t., hazy solution, trace insolubles

Mw=78,900 by GPC in FC-75 at 80° C.

Mn=23,500 by GPC in FC-75 at 80° C.

Melt index$_{120° C., 5 kg}$=8 g/min

Tg=26° C. (second heat) by DSC @10° C./min under $N_2$

10% weight loss temperature 380° C. @10° C./min under $N_2$

Tm, none detected by DSC @10° C./min, $N_2$, second heat

~5 mole % $CH_2=CHO(C=O)CF_3$ by $^{19}F$ NMR in melt

~41 mole % HFP by $^{19}F$ NMR in melt

~54 mole % TFE by $^{19}F$ NMR in melt

Productivity 4.0 kg/L/hr (33 lbs/gal/hr)

EXAMPLE 97

Continuous Polymerization in 10 ml Autoclave with Agitation HFP/TFE/$CH_2=CHCF_2CF_2CF_3$ The same set up was used as in Example 1. A mixture of 2000 g of HFP, 114 g TFE, 10 ml (14.4 g) perfluorobutylethylene, and ~1.2 g of $NF_3$ was made in 1 gallon reservoir (2). About 1777 g of this mixture were run through the 10 ml shaken autoclave at 250° C. and 14,000 psi over a 135 minute period. Drying the product under vacuum gave 51.8 g of white polymer, a 10.13 g sample of which was dried further for 4 hours at 150° C. under vacuum, giving 8.75 g of colorless polymer. Analysis results for the oven dried 8.75 g sample are gathered below.

1 g/5 ml FC-75 at r.t., hazy solution, trace insolubles

Mw=53,000 by GPC in FC-75 at 80° C.

Mn=22,700 by GPC in FC-75 at 80° C.

Tg=17° C. (second heat) by DSC @10° C./min under $N_2$

10% weight loss temperature 390° C. @10° C./min under $N_2$

Tm, none detected by DSC @10° C./min, $N_2$, second heat 4 mole % $CF_3CF_2CF_2CF_2CH=CH_2$ by $^{19}F$ NMR in melt at 320° C.

37 mole % HFP by $^{19}F$ NMR in melt at 320° C.

59 mole % TFE by $^{19}F$ NMR in melt at 320° C.

Productivity 2.0 kg/L/hr (17 lbs/gal/hr)

EXAMPLE 98

Continuous Polymerization in 10 ml Autoclave with Agitation HFP/TFE/$CH_2=CH_2$

The same set up was used as in Example 1. A mixture of 2000 g of HFP, 113 g TFE, 8 g ethylene, and ~1.2 g of $NF_3$ was made in 1 gallon reservoir (2). About 1533 g of this mixture were run through the 10 ml shaken autoclave at 250° C. and 14,000 psi over a 143 minute period. Drying the product under vacuum gave 93.8 g of white polymer, a 10.78 g sample of which was dried further for 4 hours at 150° C. under vacuum, giving 10.45 g of colorless polymer. Results for the oven dried 10.45 g sample are gathered below.

1 g/5 ml FC-75 at r.t., hazy, low viscosity solution

Mw=61,600 by GPC in FC-75 at 80° C.

Mn=19,000 by GPC in FC-75 at 80° C.

Melt index$_{120° C., 5 kg}$=2.7 g/min

Tg=23° C. (second heat) by DSC @10° C./min under $N_2$

10% weight loss temperature, 380° C. @10° C./min under $N_2$

Tm, none detected by DSC @10° C./min under $N_2$ 15.4 mole % ethylene by $^{13}C$ NMR in solution 40.2 mole % HFP by $^{13}C$ NMR in solution 44.4 mole % TFE by $^{13}C$ NMR in solution Productivity 3.8 kg/L/hr (32 lbs/gal/hr)

EXAMPLE 99

Continuous Polymerization in 10 ml Autoclave with Agitation HFP/TFE/$CH_2=CHCH_3$ The same set up was used as in Example 1. A mixture of 2000 g of HFP, 114 g TFE, 8 g propylene, and ~1.2 g of $NF_3$ was made in 1 gallon reservoir (2). About 1616 g of this mixture were run through the 10 ml shaken autoclave at 250° C. and 14,000 psi over a 150 minute period. Drying the product for 4 hours under vacuum at 150° C. gave 25.4 g of pale yellow grease/oil.

1 g/5 to 10 ml FC-75 at r.t., clear solution

Mw=9,350 by GPC in FC-75 at 80° C.

Mn=4,220 by GPC in FC-75 at 80° C.

Tg=−23.7° C. (second heat) by DSC @10° C./min under N$_2$
Tm, none detected by DSC @10° C./min, N$_2$, second heat
TGA, 10° C./min., N$_2$, 10% weight loss at, ~150° C.
Productivity 1.0 kg/L/hr (8.4 lbs/gal/hr)
Elemental Analysis, Found: 1.68% H, 1.68% H Calc.:*
(TFE)$_{-1.28x}$(HFP)$_{-1.28x}$(C$_3$H$_6$)$_x$ 1.67% H
*1:1 HFP: TFE ratio assumed

EXAMPLE 100

Continuous Polymerization in 10 ml Autoclave with Agitation HFP/TFE/CH$_2$=CHCF$_3$ The same set up was used as in Example 1. A mixture of 2000 g of HFP, 105 g TFE, 10 g 3,3,3-trifluoropropene, and ~1.2 g of NF$_3$ was made in 1 gallon reservoir (2). About 1855 g of this mixture were run through the 10 ml shaken autoclave at 250° C. and 14,000 psi over a 160 minute period. Drying the product under vacuum for 4 hours at 150° C. gave 98.8 g of a fused mass that hardened on cooling.

1 g/5 to 10 ml FC-75 at r.t., clear solution
Mw=35,000 by GPC in FC-75 at 80° C.
Mn=13,800 by GPC in FC-75 at 80° C.
Tg=13° C. (second heat) by DSC @10° C./min under N$_2$
10% weight loss temperature 390° C. @10° C./min under N$_2$
Tm, none detected by DSC @10° C./min, N$_2$, second heat
7 mole % CF$_3$CH=CH$_2$ by $^{19}$F NMR in melt at 320° C.
38 mole % HFP by $^{19}$F NMR in melt at 320° C.
55 mole % TFE by $^{19}$F NMR in melt at 320° C.
Productivity 3.7 kg/L/hr (31 lbs/gal/hr)

EXAMPLE 101

Continuous Polymerization in 10 ml Autoclave with Agitation HFP/TFE/CH$_2$=CFCF$_3$ The same set up was used as in Example 1. A mixture of 2000 g of HFP, 112 g TFE, 10 g 2,3,3,3-tetrafluoropropene, and ~1.2 g of NF$_3$ was made in 1 gallon reservoir (2). About 1652 g of this mixture were run through the 10 ml shaken autoclave at 250° C. and 14,000 psi over a 151 minute period. Drying the product for 4 hours at 150° C. under vacuum gave 74.8 g of colorless polymer.

1 g/5 ml FC-75 at r.t., clear solution
Mw=42,900 by GPC in FC-75 at 80° C.
Mn=18,600 by GPC in FC-75 at 80° C.
Tg=17° C. (second heat) by DSC @10° C./min under N$_2$
10% weight loss temperature 380° C. @10° C./min under N$_2$
Tm, none detected by DSC @10° C./min, N$_2$, second heat
8.6 mole % CF$_3$CF=CH$_2$ $^{13}$C NMR in hexafluorobenzene @60° C.
36.2 mole % HFP by $^{13}$C NMR in hexafluorobenzene solution @60° C.
55.2 mole % TFE by $^{13}$C NMR in hexafluorobenzene solution @60° C.
Productivity 3.0 kg/L/hr (25 lbs/gal/hr)

EXAMPLE 102

Continuous Polymerization in 10 ml Autoclave with Agitation HFP/TFE/CH$_2$=C(CH$_3$)$_2$ The same set up was used as in Example 1. A mixture of 2000 g of HFP, 113 g TFE, 8 g isobutylene, and ~1.2 g of NF$_3$ was made in 1 gallon reservoir (2). About 1616 g of this mixture were run through the 10 ml shaken autoclave at 250° C. and 14,000 psi over a 150 minute period. Drying the product for 4 hours under vacuum at 150° C. gave 34.8 g of yellow grease.

1 g/5 to 10 ml CF$_3$CFHCFHCF$_2$CF$_3$ at r.t., largely soluble
Mw=12,500 by GPC in FC-75 at 80° C.
Mn=4,690 by GPC in FC-75 at 80° C.
Tg=−12.6° C. (second heat) by DSC @10° C./min under N$_2$
TGA, 10° C./min., N$_2$, 10% weight loss at ~130° C.
Tm, none detected by DSC @10° C./min, N$_2$, second heat
Productivity 1.3 kg/L/hr (11 lbs/gal/hr)
Elemental Analysis, Found: 1.89% H, 1.78% H calc.:*
(TFE)$_{-1.52x}$(HFP)$_{1.52x}$(C$_4$H$_8$)$_x$ 1.84% H
*1:1 HFP: TFE ratio assumed

EXAMPLE 103

Continuous Polymerization in 10 ml Autoclave with Agitation

HFP/TFE/CH$_3$CH$_2$CH$_2$CH$_2$OCF=CF$_2$

The same set up was used as in Example 1. A mixture of 2000 g of HFP, 111 g TFE, 10 g n-butyl trifluorovinyl ether, and ~1.2 g of NF$_3$ was made in 1 gallon reservoir (2). About 1748 g of this, mixture were run through the 10 ml shaken autoclave at 250° C. and 14,000 psi over a 150 minute period. Drying the product for 4 hours under vacuum at 150° C. gave 28.8 g of orange grease.

1 g/5 to 10 ml FC-75 at r.t., opalescent solution
Mw=17,500 by GPC in FC-75 at 80° C.
Mn=6,890 by GPC in FC-75 at 80° C.
Tg=−3° C. (second heat) by DSC @10° C./min under N$_2$
TGA, 10° C./min., N$_2$, 10% weight loss at ~150° C.
Tm, none detected by DSC @10° C./min, N$_2$, second heat
Productivity 1.1 kg/L/hr (9.6 lbs/gal/hr)
Elemental Analysis, Found: 0.62% H, 0.65% H Calc:*
(TFE)$_{-5x}$(HFP)$_{-5x}$(C$_6$H$_9$F$_3$O)$_x$ 0.64% H
*1:1 HFP: TFE ratio assumed

EXAMPLE 104

Continuous Polymerization in 10 ml Autoclave with Agitation HFP/TFE/CH$_2$=CHCF$_2$CF$_2$Br The same set up was used as in Example 1. A mixture of 2000 g of HFP, 114 g TFE, 14.5 g 4-bromo-3,3,4,4-tetrafluoro-1-butene, and ~1.2 g of NF$_3$ was made in 1 gallon reservoir (2). About 1678 g of this mixture were run through the 10 ml shaken autoclave at 250° C. and 14,000 psi over a 164 minute period. Drying the product under vacuum gave 86.7 g of off-white polymer, a 10.45 g sample of which was dried furthur for 4 hours at 150° C. under vacuum, giving 8.9 g of colorless polymer. Results for the oven dried 8.9 g sample are gathered below.

1 g/5 ml FC-75 at r.t., clear solution
Mw=20,300 by GPC in FC-75 at 80° C.
Mn=7,290 by GPC in FC-75 at 80° C.
Tg=10° C. (second heat) by DSC @10° C./min under N$_2$
10% wt. loss in TGA @10° C./min under N$_2$: 320° C.
Tm, none detected by DSC @10° C./min, N$_2$, second heat
Productivity 2.7 kg/L/hr (22 lbs/gal/hr)

Elemental Analysis, Found: 4.10% Br, 4.07% Br Calc.:*
(TFE)$_{-7.02x}$(HFP)$_{-7.02x}$(C$_4$H$_3$F$_4$Br)$_x$ 4.07% Br

*1:1 HFP: TFE ratio and bromine only as part of original monomer assumed

EXAMPLE 105

Continuous Polymerization in 10 ml Autoclave with Agitation HFP/TFE/CH$_2$=CHOCH$_3$ The same set up was used as in Example 1. A mixture of 2000 g of HFP, 92 g TFE, 5 g methyl vinyl ether, and ~1.2 g of NF$_3$ was made in 1 gallon reservoir (2). About 1512 g of this mixture were run through the 10 ml shaken autoclave at 250° C. and 14,000 psi over a 130 minute period. Drying the product under vacuum gave 46.9 g of tacky yellow grease, a 13.44 g sample of which was dried further for 4 hours at 150° C. under vacuum, giving 11.48 g of grease unchanged in appearance. Results for the oven dried 11.48 g sample are gathered below.

1 g/5 to 7 ml CF$_3$CFHCFHCF$_2$CF$_3$ at r.t., clear solution

Mw=7,940 by GPC in FC-75 at 80° C.

Mn=4,650 by GPC in FC-75 at 80° C.

10% wt. loss in TGA @10° C./min under N$_2$: 200° C.

Productivity 1.4 kg/L/hr (12 lbs/gal/hr)

Elemental Analysis, Found: 0.94 & 0.93% H Calc.:* (TFE)$_{-2.4x}$(HFP)~2.4x(C$_3$H$_6$O)x0.92% H

*1:1 HFP: TFE ratio assumed

EXAMPLE 106

Continuous Polymerization in 10 ml Autoclave with Agitation HFP/TFE/Perfluorocyclobutene The same set up was used as in Example 1. A mixture of 2000 g of HFP, 111 g TFE, 10 g perfluorocyclobutene, and ~1.2 g of NF$_3$ was made in 1 gallon reservoir (2). About 1739 g of this mixture were run through the 10 ml shaken autoclave at 250° C. and 14,000 psi over a 145 minute period. Drying the product for 4 hours under vacuum at 150° C. gave 91.6 g of colorless polymer.

1 g/5 ml FC-75 at r.t., viscous hazy solution, some flocculent solids

Mw=213,000 by GPC in FC-75 at 80° C.

Mn=78,600 by GPC in FC-75 at 80° C.

Melt index$_{120° C., 15 kg}$=0.8 g/min

Tg=30° C. (second heat) by DSC @10° C./min under N$_2$

10% weight loss temperature 420° C. @10° C./min under N$_2$

Tm, none detected by DSC @10° C./min, N$_2$, second heat 0.5 mole % perfluorocyclobutene by $^{19}$F NMR in melt at 320° C.

40.9 mole % HFP by $^{19}$F NMR in melt at 320° C.

58.6 mole % TFE by $^{19}$F NMR in melt at 320° C.

Productivity 3.8 kg/L/hr (31 lbs/gal/hr)

EXAMPLE 107

Continuous Polymerization in 10 ml Autoclave with Agitation HFP/TFE/Perfluorocyclopentene The same set up was used as in Example 1. A mixture of 2000 g of HFP, 137 g TFE, 20 g perfluorocyclopentene, and ~0.6 g of NF$_3$ was made in 1 gallon reservoir (2). About 1578 g of this mixture were run through the 10 ml shaken autoclave at 350° C. and 14,000 psi over a 110 minute period. Drying the product under vacuum amd then for four hours at 150° C. under vacuum gave 217.1 g of white polymer.

1 g/5 FC-75 at r.t., clear to hazy, trace flocculent solid

Mw=103,000 by GPC in FC-75 at 80° C.

Mn=30,600 by GPC in FC-75 at 80° C.

Melt index$_{120° C., 5 kg}$=1 g/min

Tg=29° C. (second heat) by DSC @10° C./min under N$_2$

10% weight loss temperature, 380° C., @10° C./min under N$_2$

Tm, none detected by DSC @10° C./min, N$_2$, second heat 0.6 mole % perfluorocyclopentene by $^{19}$F NMR in melt at 320° C.

49.0 mole % HFP by $^{19}$F NMR in melt at 320° C.

50.4 mole % TFE by $^{19}$F NMR in melt at 320° C.

Productivity 12 kg/L/hr (98 lbs/gal/hr)

EXAMPLE 108

Continuous Polymerization in 10 ml Autoclave with Agitation HFP/TFE/Vinyl fluoride The same set up was used as in Example 1. A mixture of 2000 g of HFP, 111 g TFE, 10 g vinyl fluoride, and ~1.2 g of NF$_3$ was made in 1 gallon reservoir (2). About 1663 g of this mixture were run through the 10 ml shaken autoclave at 250° C. and 14,000 psi over a 135 minute period. Drying the product for 4 hours under vacuum at 150° C. gave 91.6 g of colorless polymer.

1 g/5 ml CF$_3$CFHCFHCF$_2$CF$_3$ at r.t., hazy solution

Mw=31,600 by GPC in FC-75 at 80° C. (partial solubility)

Mn=12,800 by GPC in FC-75 at 80° C. (partial solubility)

Tg=9° C. (second heat) by DSC @10° C./min under N$_2$

10% weight loss temperature 370° C. @10° C./min under N$_2$

Tm, none detected by DSC @10° C./min, N$_2$, second heat 16 mole % vinyl fluoride by $^{19}$F NMR in melt at 320° C.

40 mole % HFP by $^{19}$F NMR in melt at 320° C.

44 mole % TFE by $^{19}$F NMR in melt at 320° C.

Productivity 4.1 kg/L/hr (34 lbs/gal/hr)

EXAMPLE 109

Continuous Polymerization in 10 ml Autoclave with Agitation HFP/TFE/CF$_2$=C(CF$_3$)(C=O)F The same set up was used as in Example 1. A mixture of 2000 g of HFP, 115 g TFE, 10 g CF$_2$=C(CF$_3$)(C=O)F, and ~0.6 g of NF$_3$ was made in 1 gallon reservoir (2). About 1411 g of this mixture were run through the 10 ml shaken autoclave at 300° C. and 14,000 psi over a 125 minute period. Drying the product for 4 hours under vacuum at 150° C. gave 152 g of pale yellow polymer.

1 g/5 ml FC-75 at r.t., soluble, trace flocculent solids

Mw=138,000 by GPC in FC-75 at 80° C.

Mn=50,000 by GPC in FC-75 at 80° C.

Melt index$_{120° C., 5 kg}$=0.7 g/min

Tg=36° C. (second heat) by DSC @10° C./min under N$_2$

10% weight loss temperature 390° C. @10° C./min under N$_2$

Tm, none detected by DSC @10° C./min under N$_2$

~0.1 mole % CF$_2$=C(CF$_3$)COF by $^{19}$F NMR in melt at 320° C.

48.2 mole % HFP by $^{19}$F NMR in melt at 320° C.

51.7 mole % TFE by $^{19}$F NMR in melt at 320° C.
Productivity 7.3 kg/L/hr (61 lbs/gal/hr)

EXAMPLE 110

Continuous Polymerization in 10 ml Autoclave with Agitation HFP/TFE/CF$_2$=CFH

The same set up was used as in Example 1. A mixture of 2000 g of HFP, 111 g TFE, 10 g CF$_2$=CFH, and ~1.2 g of NF$_3$ was made in 1 gallon reservoir (2). About 1622 g of this mixture were run through the 10 ml shaken autoclave at 250° C. and 14,000 psi over a 150 minute period. Drying the product for 4 hours under vacuum at 150° C. gave 109.8 g of colorless polymer.

1 g/5 ml FC-75 at r.t., clear solution, trace (?) insolubles
Mw=185,000 by GPC in FC-75 at 80° C.
Mn=71,400 by GPC in FC-75 at 80° C.
Melt index$_{120°\ C.,\ 5\ kg}$=0.3 g/min
Tg=27° C. (second heat) by DSC @10° C./min under N$_2$
10% wt. loss temperature, 420° C. @10° C./min under N$_2$
Tm, none detected by DSC @10° C./min, N$_2$, second heat
7.8 mole % CF$_2$=CFH by $^{19}$F NMR in melt at 320° C.
39.2 mole % HFP by $^{19}$F NMR in melt at 320° C.
53.0 mole % TFE by $^{19}$F NMR in melt at 320° C.
Productivity 4.4 kg/L/hr (36 lbs/gal/hr)

EXAMPLE 111

Continuous Polymerization in 10 ml Autoclave with Agitation HFP/TFE/Perfluoro-2-methylene-4-methyl-1,3-dioxolane The same set up was used as in Example 1. A mixture of 2000 g of HFP, 116 g TFE, 20 g perfluoro-2-methylene-4-methyl-1,3-dioxolane, and ~0.6 g of NF$_3$ was made in 1 gallon reservoir (2). About 1471 g of this mixture were run through the 10 ml shaken autoclave at 300° C. and 14,000 psi over a 140 minute period. Drying the product for 4 hours under vacuum at 150° C. gave 156 g of colorless polymer.

1 g/5 ml FC-75 at r.t., hazy solution, flocculent residue
Mw=108,000 by GPC in FC-75 at 80° C.
Mn=39,400 by GPC in FC-75 at 80° C.
Melt index$_{120°\ C.,\ 5\ kg}$=1.1 g/min
Tg=31° C. (second heat) by DSC @10° C./min under N$_2$
10% wt. loss temperature, 370° C. @10° C./min under N$_2$
Tm, none detected by DSC @10° C./min under N$_2$
2.3 mole % perfluoro-2-methylene-4-methyl-1,3 dioxolane by $^{19}$F NMR in melt at 320° C.

46.0 mole % HFP by $^{19}$F NMR in melt at 300° C.
51.7 mole % TFE by $^{19}$F NMR in melt at 300° C.
Productivity 6.7 kg/L/hr (56 lbs/gal/hr)

What is claimed is:

1. An amorphous polymer, consisting essentially of, repeat units of the formula:

(a) at least about 30 mole percent of

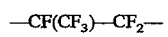
  $$—CF(CF_3)—CF_2— \qquad (I)$$

(b) at least about 1 mole percent

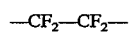
  $$—CF_2—CF_2— \qquad (II)$$

(c) 0 to about 10 mole percent

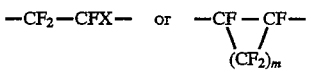
  $$—CF_2—CFX— \quad \text{or} \quad —\underset{\underset{(CF_2)_m}{\diagup}}{CF}—\underset{}{CF}— \qquad (III)$$

wherein X is —C$_n$F$_{2n+1}$ or —OC$_n$F$_{2n+1}$, m is 2, 3 or 4, and n is an integer of 2 to 20, with —C$_n$F$_{2n+1}$ or an integer of 1 to 20 with —OC$_n$F$_{2n+1}$; and provided that in said polymer less than 20 mole percent of (I) is present in the form of triads.

2. The polymer is recited in claim 1 wherein (II) is at least about 30 mole percent of said repeat unit.

3. The polymer as recited in claim 1 wherein only (I) and (II) are present.

4. The polymer as recited in claim 2 wherein (II) is about 50 to about 65 mole percent of said repeat units.

5. The polymer as recited in claim 1 wherein (III) is about 0.1 to about 10 mole percent of said repeat units.

6. The polymer as recited in claim 5 wherein (I) is about 50 to about 65 mole percent of said repeat units.

7. The polymer as recited in claim 5 wherein X is —C$_n$F$_{2n+1}$, wherein n is 2 to 4.

8. The polymer as recited in claim 5 wherein X is —OC$_n$F$_{2n+1}$, and n is an integer of 1 to 4.

9. The polymer as recited in claim 1 wherein less than about 15 mole percent of (I) is present in the form of triads.

10. The polymer as recited in claim 1 wherein less than about 10 mole percent of (I) is present in the form of triads.

11. The polymer as recited in claim 2 wherein less than about 15 mole percent of (I) is present in the form of triads.

12. The polymer as recited in claim 1 which has a molecular weight distribution of about 4 or less.

* * * * *